United States Patent
Liang et al.

(10) Patent No.: US 9,404,131 B2
(45) Date of Patent: Aug. 2, 2016

(54) PROCESS FOR THE PREPARATION OF INGENOL-3-ANGELATE

(71) Applicant: LEO Laboratories Limited, Dublin (IE)

(72) Inventors: Xifu Liang, Ballerup (DK); Thomas Hogberg, Ballerup (DK); Gunnar Grue-Sorensen, Roskilde (DK); Thomas S. Moody, Craigavon (GB); Andrew S. Rowan, Craigavon (GB)

(73) Assignee: LEO Laboratories Limited, Dublin (IE)

( * ) Notice: Subject to any disclaimer, the term of this patent is extended or adjusted under 35 U.S.C. 154(b) by 0 days.

(21) Appl. No.: 14/341,720

(22) Filed: Jul. 25, 2014

(65) Prior Publication Data

US 2015/0024443 A1    Jan. 22, 2015

Related U.S. Application Data

(63) Continuation of application No. PCT/EP2013/051431, filed on Jan. 25, 2013.

(60) Provisional application No. 61/669,657, filed on Jul. 9, 2012, provisional application No. 61/590,544, filed on Jan. 25, 2012.

(51) Int. Cl.
*C12P 7/62* (2006.01)
*C12P 15/00* (2006.01)

(52) U.S. Cl.
CPC . *C12P 7/62* (2013.01); *C12P 15/00* (2013.01); *C12Y 301/01003* (2013.01); *Y02P 20/52* (2015.11)

(58) Field of Classification Search
CPC ........................................... C12P 15/00
See application file for complete search history.

(56) References Cited

U.S. PATENT DOCUMENTS

2013/0177952 A1    7/2013   Hogberg et al.

FOREIGN PATENT DOCUMENTS

| WO | 2012/010172 A1 | 1/2012 |
| WO | 2013/110753 A1 | 8/2013 |

OTHER PUBLICATIONS

Teng et al., Fitoterapia, 80(4):233-236 (2009).
Abo et al., Phylochemistry 21(3): 725-726 (1982).
Opferkuch et al., Zeitschrift für Naturforschung, 36b:878-887 (1981).
Sorg et al.,37b:748-756 (1982).
International Search Report and Written Opinion dated Jun. 19, 2013 in corresponding PCT Application No. PCT/EP2013/051431.

*Primary Examiner* — Bin Shen
(74) *Attorney, Agent, or Firm* — Fish & Richardson P.C.

(57) ABSTRACT

The invention relates to methods for preparing ingenol-3-angelate from ingenol or ingenol derivatives.

27 Claims, 1 Drawing Sheet

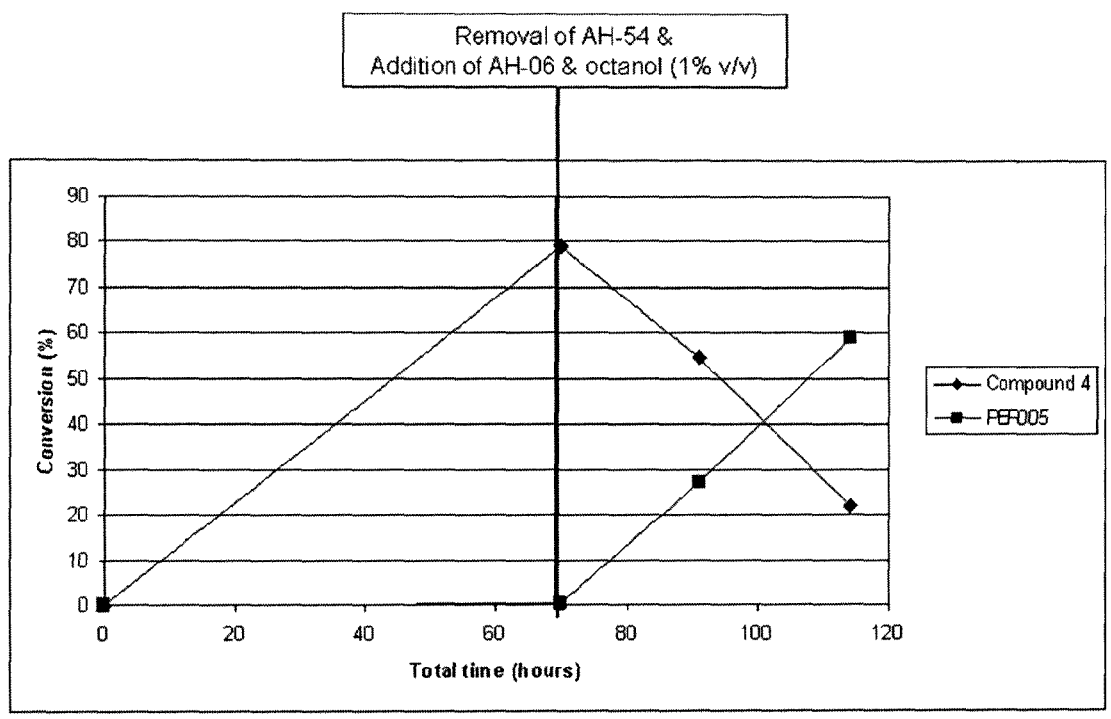

PROCESS FOR THE PREPARATION OF INGENOL-3-ANGELATE

RELATED APPLICATIONS

This application is a continuation of PCT International Patent Application No. PCT/EP2013/051431, filed Jan. 25, 2013, which claims the benefit of and priority to U.S. Provisional Application Nos. 61/590,544, filed Jan. 25, 2012, and 61/669,657, filed Jul. 9, 2012. The entire contents of each of the foregoing applications are expressly incorporated herein by reference.

The invention provides a process for preparing ingenol-3-angelate from Ingenol.

BACKGROUND OF THE INVENTION

Ingenol-3-angelate has been described previously as being useful in treating a number of disorders, in particular actinic keratosis. The compound can be isolated from a natural source, and is present in relatively small amount in plants of the *Euphorbia* plant family. The related compound, ingenol, however, can be isolated from natural sources in larger quantities. The present invention thus provides a process for preparing ingenol-3-angelate starting from ingenol.

SUMMARY OF THE INVENTION

The present invention provides a process wherein ingenol-3-angelate (also referred to herein as "PEP005") is synthesized from ingenol in a process containing at least one enzyme assisted step.

The invention provides in an embodiment a method for preparation of ingenol-3-angelate comprising acylation of ingenol, optionally followed by deacylation of a di-acylated ingenol derivative, wherein at least one step is catalysed by an enzyme.

The present invention provides a one, two or a three step reaction for preparation of ingenol-3-angelate from ingenol comprising at least one enzyme catalyzed reaction.

The invention provides a method for preparation of ingenol-3-angelate comprising deacylation of a di-acylated ingenol derivative by catalysis by an enzyme.

The invention provides a method as above wherein the diacylated compound is ingenol-3,20-di-angelate.

The invention provides a method as above wherein the diacylated compound contains an acyl group in position 20, which is different from angeloyl.

The invention provides a method as above wherein the acyl group in position 20 is R—C=O— and R is selected from substituted or unsubstituted $C_1$-$C_{10}$-alkyl wherein the alkyl can be straight or branched, substituted or unsubstituted $C_2$-$C_{10}$-alkenyl, or substituted or unsubstituted $C_4$-$C_7$-cyclic alkyl, substituted or unsubstituted aryl or substituted or unsubstituted heteroaryl.

The invention provides the compounds ingenol-3,20-di-angelate and 3-O-angeloyl-20-O-acetyl-ingenol, and the ingenol compound containing an acyl group in position 20, which is different from angeloyl, such as those mentioned above. The invention provides the compounds and their use as intermediates in a method for preparation of ingenol-3-angelate as described above.

The invention provides a method as above wherein the enzymes are Lipase A or Lipase B from *Candida rugosa*.

The invention provides a method as above wherein the reaction is performed in heptane or MTBE.

The invention provides a method as above wherein the solvent is heptane.

The invention provides a method as above wherein the reaction is performed in the presence of a nucleophile.

The invention provides a method as above wherein the nucleophile is an alcohol.

The invention provides a method as above wherein the alcohol is selected from 1-butanol, 1-pentanol, 1-hexanol and 1-octanol The invention provides a method as any of the above wherein the nucleophile is present in a concentration below about 2.5% v/v.

The invention provides a method as above wherein the nucleophile is present in a concentration of about 1% v/v.

The invention provides a method as any of the above wherein the enzyme is Lipase A from *Candida rugosa*, the solvent is heptane, the nucleophile is 1-butanol, 1-pentanol, 1-hexanol or 1-octanol at a concentration of about 1% v/v.

The invention provides a method for the preparation of the diacylated ingenol derivative comprising reaction ingenol in the presence of an acyldonor and optionally enzymes.

The invention provides a method as above wherein the acyl donor is angelic anhydride.

The invention provides a method as above wherein the acyl donor is added in 4 equivalents.

The invention provides a method as above wherein the enzymes are selected from Lipases A, B, C, D, E or F from *Alcaligenes* sp., Lipase from *Pseudomonias stutzeri*, Lipase from *Pseudomonas cepacia*, Lipase A or B from *Candida rugosa*, Lipase from *Carica Papaya*, Lipase from *Penicillum camembertii*, Protease C from *Bacillus subtilis*, Lipase from *Pseudomonas fluorescens*, Lipases A and B from *Burkholderia cepacia*, or ficin.

The invention provides a method as above wherein the enzymes are Lipase A, C or E from *Alcaligenes* sp.

The invention provides a method as above wherein the reaction is performed in organic solvent.

The invention provides a method as above wherein the solvent is heptane or hexane.

The invention provides a method as any the above wherein the reaction is performed at elevated temperatures.

The invention provides a method as above wherein the temperature is about 50° C.

The invention provides a method for the preparation of ingenol-3-angelate from ingenol with an acyldonor in a one step reaction catalyzed by enzymes.

The invention provides a method as above wherein the reaction utilizes angelic anhydride as acyl donor.

The invention provides a method as above wherein the enzymes are the hydrolases Lipase from *Carica Papaya*, Lipase from *Penicillum camembertii*, Protease C from *Bacillus subtilis*, Lipases A and B from *Burkholderia cepacia*, ficin, or Lipobond *P. Cepacia*.

The invention provides a method as above wherein the enzyme is Lipobond *P. Cepacia*.

The invention provides a method as above wherein the solvent is acetonitrile.

The invention provides a method as above wherein the reaction mixture contains surfactant.

The invention provides a method as above, wherein the surfactant is selected from CTAC, TTAB, CPC, BZT, BAC, DDAC, DDAB.

The invention provides a method as above wherein the surfactant is CPC or BZT.

BRIEF DESCRIPTION OF THE DRAWINGS

FIG. 1: A plot of total reaction time versus % conversion for the one-pot synthesis of ingenol-3-angelate via initial synthesis of ingenol-3,20-diangelate in heptane.

DETAILED DESCRIPTION OF THE INVENTION

The present invention utilizes enzymes in the process of manufacturing ingenol-3-angelate from ingenol. Enzymes have the ability to catalyze chemical reactions in a specific manner. This characteristic proves valuable in the present invention, since not only ingenol but also ingenol-3-angelate has a number of stereocenters but ingenol itself has also a total of 4 hydroxy groups. Two of these hydroxy groups are secondary alcohols and of comparable reactivity. However, only the 3-position in ingenol should be derivatised with an angeloyl group in ingenol-3-angelate. Additionally, ingenol also contains a primary alcohol, which should not react with the angeloyl moiety, but often primary alcohols are very reactive. Also a tertiary alcohol is present, which is not to be derivatised. While chemically it may be difficult to specifically derivatise one hydroxyl-group and not the others, enzymes have now been shown to be able to catalyse such reactions in a specific manner.

The present invention provides a hydrolase catalyzed selective acylation of ingenol to ingenol-3-angelate in either one, two or a three step reaction.

The reaction pursued in the present invention is a hydrolase catalyzed selective acylation of ingenol. Hydrolase enzymes catalyse the hydrolysis of a chemical bond. They can be further subcatagorised according to the types of compounds they hydrolyse. Lipases catalyse the hydrolysis of ester bonds in lipids, proteases catalyse the hydrolysis of peptide bonds etc. As well as selective hydrolysis in aqueous media, hydrolases can be employed to carry out selective acylation in non-aqueous media. Enzymes can be isolated from natural sources and they can be derivatised into having suitable characteristics.

Preferably, the enzyme should be specific as to the ingenol target and the final product produced, and providing the final product in an acceptable purity and yield. Also the enzymes should be functional under conditions acceptable for a chemical reaction. Often this means organic solvent and elevated temperatures. Also for commercial product scale, the enzyme should preferably be available in larger quantities for industrial pharmaceutical use.

The methods of the present invention are outlined below:

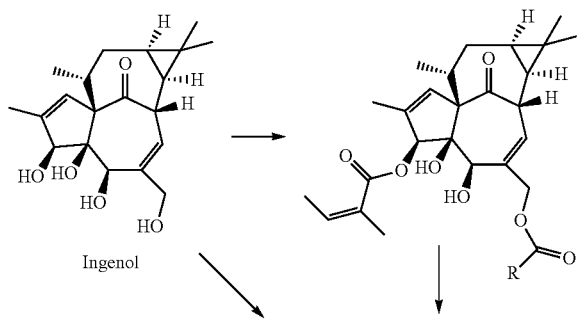

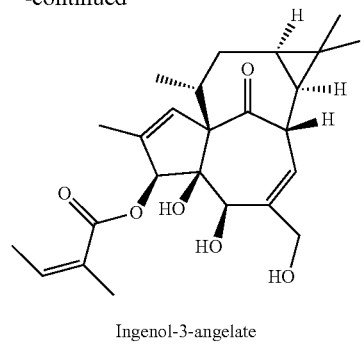

Ingenol-3-angelate

PEP005 from Diacylated Product:

Depending on the specificity of the reaction and the enzymes involved, byproducts will potentially be formed in the process.

In an embodiment of the above process, the 3- and 20-position are derivatised with angeloyl (ingenol-3,20-diangelate above). In another embodiment, the hydroxyl group in 20-position is derivatised with a group different from angeloyl.

In an embodiment R—(C=O)—O— group as illustrated above includes substituted or unsubstituted $C_1$-$C_{10}$-alkyl-carboxylic acid esters wherein the alkyl can be straight or branched, substituted or unsubstituted $C_2$-$C_{10}$-alkenyl-carboxylic acid esters, or substituted or unsubstituted $C_4$-$C_7$-cyclic aliphatic carboxylic acid esters, substituted or unsubstituted aromatic carboxcylic acid ester or substituted or unsubstituted heteroaromatic carboxcylic acid esters. In an embodiment the R—(C=O)—O is selected from formate, acetate, propionate, butyrate, pivaloate, crotonate, angelate, 4-pentenoate, chloroacetate, dichloroacetate, trifluoroacetate, methoxyacetate, penoxyacetate, benzoate, penylacetate, 3-phenylpropionate, 4-oxopentanoate, 4-methoxycrotonate, or p-phenylbenzoate. In an embodiment the group is selected from acetate, butyrate, pivaloate or benzoate, 4-oxopentanate.

In the context of the present invention the $C_1$-$C_{10}$-alkyl includes the straight and branched alkyl such as methyl, ethyl, propyl, butyl, 2-butyl, tert-butyl, 1-pentyl, 2-pentyl, 3-pentyl etc., hexyl, heptyl, octyl, nonyl, dodecanyl. In the context of the present invention the $C_2$-$C_{10}$-alkenyl are for example selected from ethenyl, propenyl, 2-butenyl, 1-butenyl, angelyl, 4-pentenyl. In the context of the present invention aryl is phenyl, benzyl, or naphtyl. In the context of the present invention heteroaryl is aryl as defined above including one or more heteroatoms. In the context of the present invention the substituted variants include for example $C_4$-$C_7$-cycloalkylmethyl, $C_4$-$C_7$-cycloalkylethyl, or halogen substitution such as chloromethyl, chloroethyl, dichloromethyl, dichloroethyl, fluoromethyl, fluoroethyl, difluoromethyl, difluoroethyl, trifluoromethyl, trifluoroethyl, or ether derivatives such as methoxymethyl, methoxyethyl, phenoxymethyl, phenoxyethyl, 3-methoxypropenyl, phenylsubstited derivatives such as benzyl, phenylethyl, 3-phenylpropyl, p-diphenyl, p-phenyl-benzyl, or oxo variants such as 3-oxo-butyl.

If the two groups in position 3 and position 20 are different, an additional process step may be required. The derivatisation can be performed chemically or enzyme catalyzed. After either of the methods, the invention describes a specific deacylation of position 20 to provide ingenol-3-angelate.

In one embodiment the deacylation proceeds from the ingenol-3,20-diangelate.

The enzymes capable of deacylating specifically from position 20 were Lipase A or Lipase B from *Candida rugosa*.

The reaction proceeds in organic solvents such as acetonitrile, heptane or MTBE. In embodiments of the invention the solvent is heptane or MTBE.

In an embodiment of the invention, the deacylation reaction contains a nucleophile, such as an alcohol. In the context of the present invention alcohols are lower alcohols such as $C_{1-10}$-alkyl-OH, including all the isomers. Non limiting examples are methanol, ethanol, propanol, isopropanol, butanol, 2-butanol, tert-butanol, 1-pentanol, 2-pentanol, 3-pentanol etc. Suitable alcohols are butanol, pentanol, hexanol and octanol. In the context of the present invention butanol means 1-butanol, hexanol means 1-hexanol, and octanol means 1-octanol unless specified otherwise. In embodiments of the invention mixtures of the alcohols are added to the reaction mixture. In embodiments of the invention the alcohol is present in the reaction mixture in a concentration below 2.5%. In embodiments of the invention the alcohol is present in the reaction mixture in a concentration below 1%.

In an embodiment of the invention the reaction is water free to prevent a potential migration of the acyl group from position 3 to position 5 or position 20 in water.

Formation of the Diacylated Product:

Dependent upon the choice of the diacylated product, ie. the positions 3 and 20 can be derivatised with identical or different acyl groups, the formation of the diacylated product from ingenol, may be performed in a one- or two-step reaction.

When preparing a diacylated product from ingenol, the monoacylated products may also be formed. These may have an undesired substitution pattern for the present invention. Predominant products obtained were:

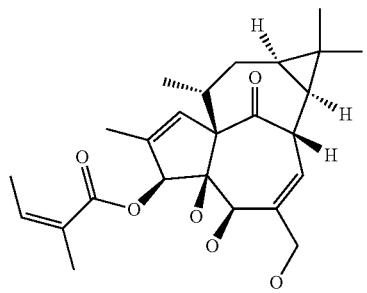

Ingenol-3-angelate
PEP005

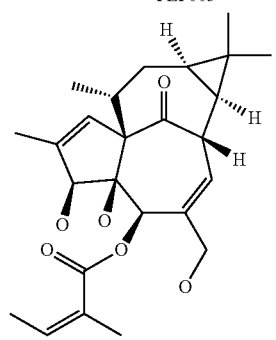

Ingenol-5-angelate
PEP015

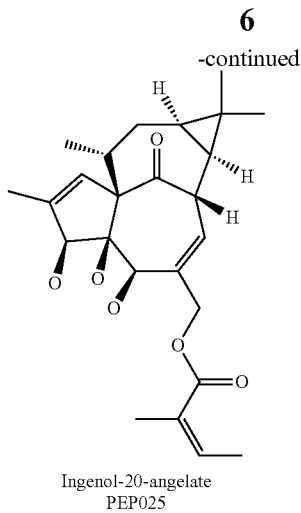

Ingenol-20-angelate
PEP025

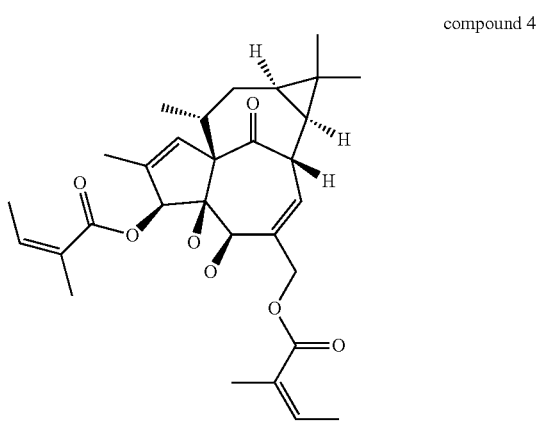

compound 4

Ingenol-3,20-diangelate

Potential byproducts are also ingenol-3,5-diangelate, and ingenol-3,5,20-triangelate.

It is an object of the present invention to provide a selective process for formation of a diacylated ingenol suitable for selective deacylation to ingenol-3-angelate, by the use of biocatalysis in the form of enzymes in at least one step.

The one step reaction, derivatising with the angeloyl donor, may form different products: ingenol 3-angelate, PEP025, PEP015, and the diacylated and triacylated derivatives. Of the products potentially formed it is desirable to obtain the monoacylated product ingenol-3-angelate, or the diacylated product ingenol-3,20-diangelate. The 3-monoacylated product is the desired product for the process as such, whereas the diacylated derivative, ingenol-3,20-diangelate, can be deacylated as described. Other by-products are not desired for the current process and the invention discloses processes which specifically produces the desired products. A byproduct such as the PEP015 or PEP025 may eventually be hydrolysed into ingenol, which is the starting material for the process. If this reaction cycle were to be performed, and optimization could then recover the byproducts, hydrolyse and recycle them. However, the present invention describes a process which provides acceptable yields of the desired products over the byproducts.

A one step reaction is performed with one acyldonor as mentioned below:

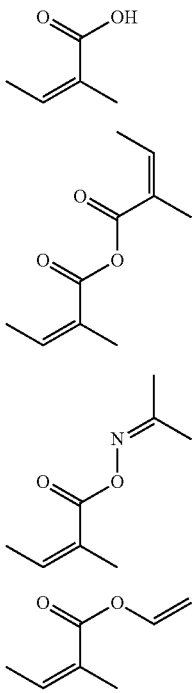

In an embodiment the acyldonor is angelic anhydride or the oxime 3. In an embodiment of the invention the acyldonor is angelic anhydride. In general it is observed that a surplus of acyldonor provides improved yields of the diacylated product. However, a balance of the cost of the intermediates over the yields must be evaluated.

In an embodiment of the invention, the angelic anhydride is added in no less than 2 equivalents. In an embodiment 2.5 equivalents or more of angelic anhydride is added to the ingenol. In an embodiment the angelic anhydride is added in 4 equivalents or more to the ingenol.

The reaction proceeds to the desired products when the enzymes are selected from Lipases A, B, C, D, E or F from *Alcaligenes* sp., Lipase from *Pseudomonias stutzeri*, Lipase from *Pseudomonas cepacia*, Lipase A or B from *Candida rugosa*, Lipase from *Carica Papaya*, Lipase from *Penicillum camembertii*, Protease C from *Bacillus subtilis*, Lipase from *Pseudomonas fluorescens*, Lipases A and B from *Burkholderia cepacia*, or ficin.

In an embodiment the enzymes are selected from Lipases A, B, C and E from *Alcaligenes* sp., Lipase from *Pseudomonas cepacia*, Lipase B from *Candida rugosa*, Lipase from *Penicillum cannennbertii*, Lipases A and B from *Burkholderia cepacia*.

In an embodiment the enzymes are selected from Lipases A, C and E from *Alcaligenes* sp.

In an embodiment the solvent is toluene, hexane or heptane. In an embodiment the solvent is hexane or heptane.

Optimisation of temperature on the reactions may be dependent on the enzymes. However, the experiments performed in the present invention indicated a clearly increased yield of the diacylated product at higher temperatures. In an embodiment the temperature of the reaction is about 50° C., or higher.

In an embodiment of the invention the reaction is performed with lipase A from *alcaligenes* sp. with 4 equivalents of angelic anhydride at 50° C. in heptane.

In an embodiment of the invention, ingenol is derivatised into 20-acetyl-ingenol. This reaction is performed either chemically or by the use of enzymes. The 20 position of ingenol is a primary alcohol, which is the most reactive of the alcohols in ingenol, and therefore this product can be obtained in high yields in a very specific reaction. Secondly, this compound is further derivatised in a reaction using the angeloyl donor compound optionally by the use of enzymes as catalysts. A selective deacetylation of the 20-position will provide PEP005.

PEP005 from Ingenol in One Step

In an embodiment the method of the present invention is outlined below:

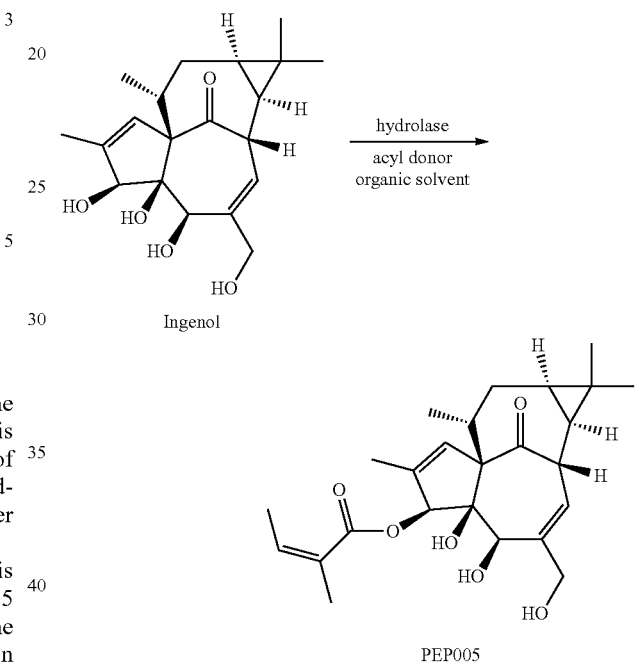

The reaction conditions are selected to minimize formation of undesired by-products and diacylated product, whereby ingenol-3-angelate is formed in a one step process.

The process for preparation of ingenol-3-angelate can utilize a number of different angeloyl sources such as the following:

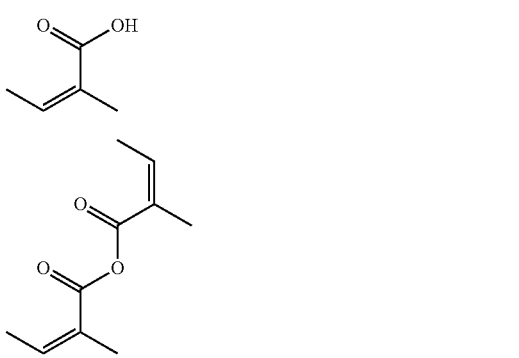

-continued

3

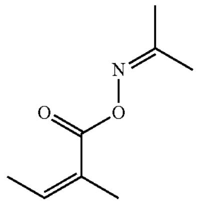

5

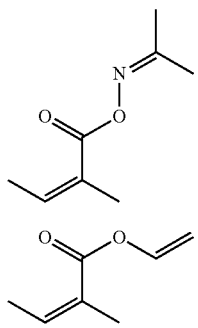
Of the selected acyldonors, compounds 2 and 3 were suitable as acyldonors.

The enzymes capable of catalyzing the monoacylation in position 3 of ingenol to form ingenol-3-angelate was the enzyme characterised by the reaction utilizes angelic anhydride 2 as acyl donor with hydrolases Lipase from *Carica Papaya*, Lipase from *Penicillum camembertii*, Protease C from *Bacillus subtilis*, Lipases A and B from *Burkholderia cepacia*, ficin, or Lipobond *P. Cepacia*. In an embodiment of the invention the enzyme is Lipobond *P. Cepacia.*

The reaction was performed in acetonitrile as solvent.

Surfactants are compounds that can influence the microenvironment of an enzyme, enhancing its activity and selectivity The tested surfactants were the anionic surfactant dioctyl sodium sulfosuccinate (AOT), cationic surfactant CTAB and non-ionic polysorbate surfactant Tween-20. Additional surfactants are: cetyl trimethylammonium chloride (CTAC), Tetradecyl trimethylammonium bromid (TTAB), Cetylpyridinium chloride (CPC), Benzethonium chloride (BZT), Benzalkonium chloride (BAC), dimethyldioctadecylammonium chloride (DDAC), dimethyldioctadecylammonium bromide (DDAB), and cetyl trimethylammonium bromide (CTAB).

A 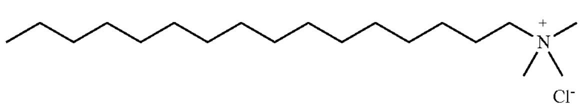 cetyl trimethylammonium chloride (CTAC)

B

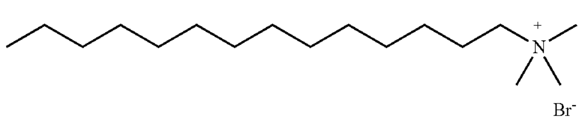

Tetradecyl trimethylammonium bromide (TTAB)

C

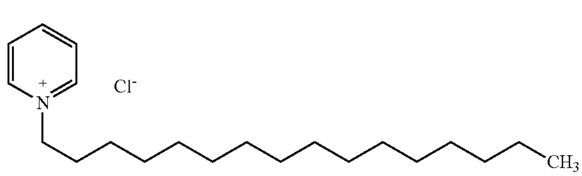

Cetylpyridinium chloride (CPC)

-continued

D

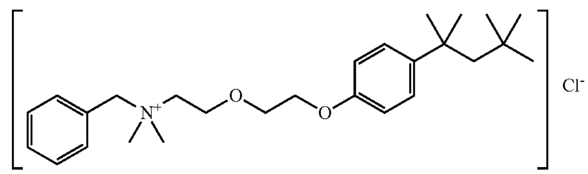

Benzethonium chloride (BZT)

E

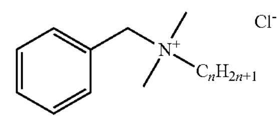

*n* = 8, 10, 12, 14, 16, 18
Benzalkonium chloride (BAC)

F

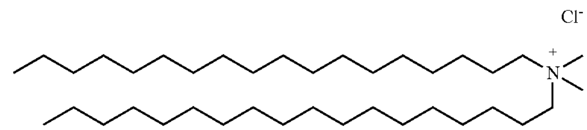

Dimethyldioctadecylammonium chloride (DDAC)

G

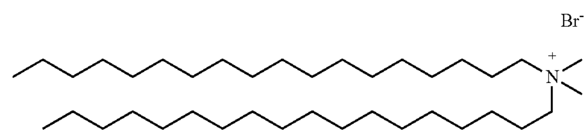

Dimethyldioctadecylammonium bromide (DDAB)

H 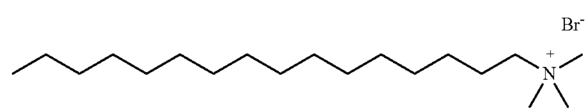 cetyl trimethylammonium bromide (CTAB)

In an embodiment the reaction mixture contains surfactant. In an embodiment the surfactant is selected from CTAC, TTAB, CPC, BZT, BAC, DDAC, DDAB. In an embodiment the surfactant is CPC or BZT.

EXAMPLES

TABLE 1

| Hydrolase enzymes | |
|---|---|
| Code | Enzyme Type |
| 1 | Lipase A from *Alcaligenes* sp. |
| 02 | Lipase B from *Alcaligenes* sp. |
| 03 | Lipase C from *Alcaligenes* sp. |
| 04 | Lipase from *Pseudomonas Stutzeri* |
| 05 | Lipase from *Pseudomonas cepacia* |
| 06 | Lipase A from *Candida rugosa* |
| 07 | Lipase D from *Alcaligenes* sp. |
| 08 | Lipase E from *Alcaligenes* sp. |
| 09 | Lipase B from *Candida rugosa* |
| 10 | Lipase F from *Alcaligenes* sp. |
| 17 | Lipase from *Carica papaya* |
| 24 | Lipase B from *Candida rugosa* |
| 32 | Lipase from *Penicillium camambertii* |
| 33 | Protease C from *Bacillus subtilis* |
| 35 | Lipase from *Pseudomonas fluorescens* |

TABLE 1-continued

Hydrolase enzymes

| Code | Enzyme Type |
| --- | --- |
| 36 | Lipase A from *Burkholderia cepacia* |
| 37 | Lipase B from *Burkholderia cepacia* |
| 39 | Lipase from *Candida Antarctica* |
| 40 | Lipase from *Thermomyces lanuginosus* |
| 41 | Protease A from *Bacillus* sp. |
| 44 | Protease B from *Bacillus* sp. |
| 48 | Ficin |
| 49 | Lipobond CALB |
| 50 | Adsorbed CALB |
| 51 | Lipo CALB |
| 53 | Antiplus CALB |
| 54 | Lipobond *P.cepacia* |
| 55 | Epobond CALB |
| 57 | Savinase CLEA |
| 58 | Esperase CLEA |

HPLC Method:

TABLE A

Conditions for HPLC method A

| Column: | Chromolith Performance RP18e (4.6 × 100 mm, 2 μm) |
| --- | --- |
| Flow rate: | 3 mL/min |
| Eluent gradient: | Solvent A: 25 mM $KH_2PO_4$ buffer in $H_2O$ (pH 2.2) |
| | Solvent B: Acetonitrile |

| Time (mins) | % A | % B |
| --- | --- | --- |
| 0 | 80 | 20 |
| 3.5 | 20 | 80 |
| 6 | 20 | 80 |
| 6.5 | 80 | 20 |
| 8.5 | 80 | 20 |

| Detector type: | UV (PDA detection) |
| --- | --- |
| Wavelength: | 235 nm |
| Run time (mins): | 8.5 mins |

TABLE B conditions for HPLC method B.

| Column: | Chromolith Performance RP18e (4.6 × 100 mm, 2 μm) |
| --- | --- |
| Flow rate: | 3 mL/min |
| Eluent gradient: | Solvent A: 25 mM $KH_2PO_4$ buffer in $H_2O$ (pH 2.2) |
| | Solvent B: Acetonitrile |

| Time (mins) | % A | % B |
| --- | --- | --- |
| 0 | 60 | 40 |
| 5.5 | 20 | 80 |
| 8.0 | 20 | 80 |
| 8.5 | 60 | 40 |
| 10.5 | 60 | 40 |

| Detector type: | UV (PDA detection) |
| --- | --- |
| Wavelength: | 235 nm |
| Run time: | 10.5 mins |

Calculation of Relative Response Factors (RRFs)

It was known that Ingenol absorbs more weakly at 235 nm than the acylated compounds ingenol-3-angelate, PEP015, PEP025 and ingenol-3,20-diangelate. Therefore, in order to get more accurate percentage conversions for screening reactions, it was necessary to calculate relative response factors (RRFs) for each of these components.

To achieve this, HPLC samples of known concentration were prepared from stock solutions. Ingenol-3-angelate, PEP015, PEP025 and ingenol-3,20-diangelate were prepared as 10 mM solutions in DMSO—50 μL was added to 1.2 mL of an 8:2 mixture of 25 mM $KH_2PO_4$ (pH 2.2)/acetonitrile to give 0.4 mM samples. A stock solution of ingenol was prepared by dissolving 9.2 mg in 5 mL acetonitrile—200 μL of this was added to 1 mL of an 8:2 mixture of 25 mM $KH_2PO_4$ (pH 2.2)/acetonitrile to give a sample concentration of 0.7123 mM. These samples were analysed by HPLC and the peak areas used to calculate the RRFs, taking into account sample concentration and compound purities (Table 2). Response factors are given relative to ingenol-3-angelate.

(NOTE: Ingenol purity was calculated as 84.18% by quantitative $^1$H NMR. As ingenol-3-angelate, PEP015, PEP025 and ingenol-3,20-diangelate were provided as solutions in DMSO, purity was not calculated but assumed to be 100%).

TABLE 2

Calculation of RRFs for ingenol, ingenol-3-angelate, PEP015, PEP025 and ingenol-3,20-diangelate.

| COMPONENT | PURITY | SAMPLE CONC (mM) | PEAK AREA | (peak area if all samples 1 mM) PEAK AREA*100/ CONC*PURITY | RRF |
| --- | --- | --- | --- | --- | --- |
| INGENOL | 84.18 | 0.7123 | 927036 | 1546054.267 | 0.159473927 |
| PEP005 | 100 | 0.4 | 3877886 | 9694715 | 1 |
| PEP015 | 100 | 0.4 | 4432309 | 11080772.5 | 1.142970423 |
| PEP025 | 100 | 0.4 | 3038236 | 7595590 | 0.783477389 |
| COMPOUND 4 | 100 | 0.4 | 3070079 | 7675197.5 | 0.791688822 |

These RRFs were then used to calculate % conversions based on peak areas of analysed screening reactions, as shown in Table 3 heptane, visualized by phosphomolybdic acid stain and heating). Any reactions exhibiting formation of acylated product(s) were analysed by HPLC (Method A).

TABLE 3

An example of calculation of % conversions based on peak areas from HPLC analysis of a screening reaction.

| Reaction component | INGENOL | PEP005 | PEP015 | PEP025 | COMPOUND 4 |
|---|---|---|---|---|---|
| Relative response factor | 0.159473927 | 1 | 1.142970423 | 0.783477389 | 0.791688822 |
| Peak area from HPLC | 246165 | 2134040 | 477677 | 789931 | 2743221 |
| Adjusted area | 1543606.566 | 2134040 | 417925.9503 | 1008237.137 | 3465024.291 |
| Actual % | 15.8811133 | 21.9556795 | 4.299754559 | 10.37306303 | 35.64926749 |

Ingenol-3-Angelate from Ingenol

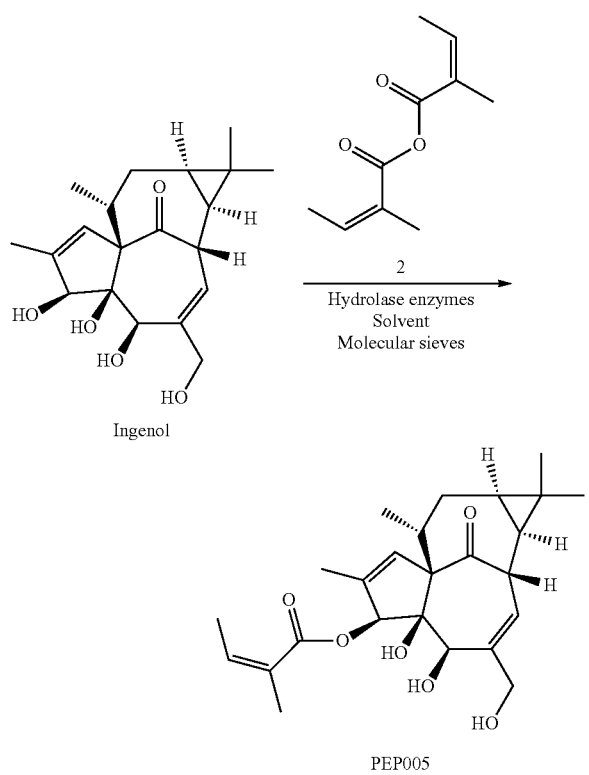

Ingenol was screened against 60 hydrolase enzymes in two different solvents (MTBE and acetonitrile) with oxime ester 3 as acyl donor. All screening reactions were carried out in HPLC vials. The general screening conditions are outlined below. Each screening reaction contained:
  2 mg Ingenol
  1.5 eq. angelic anhydride
  1 small scoop of enzyme (if solid) or 2 drops (if liquid) (~10 mg)
  2 or 3 pellets of 4 Å molecular sieves
  0.5 mL solvent Enzyme and molecular sieves were added to the reaction vial first, followed by 0.5 mL of a stock solution of Ingenol and oxime ester 3 in reaction solvent.

Screening reactions were shaken at room temperature for 112 hours and then analysed by TLC (eluent 1:1 EtOAc/heptane, visualized by phosphomolybdic acid stain and heating). Any reactions exhibiting formation of acylated product(s) were analysed by HPLC (Method A).

HPLC samples were prepared by adding 100 μL of reaction mixture to a glass pipette containing a cotton wool plug and washing through with ~1.2 mL of an 8:2 mixture of 25 mM $KH_2PO_4$ buffer (pH 2.2)/acetonitrile.

Screening with Angelic Anhydride as Acyl Donor

All screening reactions were carried out in HPLC vials. The general screening conditions are outlined below. Each screening reaction contained:
  2 mg Ingenol
  1.5 eq. acyl donor
  1 small scoop of enzyme (if solid) or 2 drops (if liquid) (~10 mg)
  2 or 3 pellets of 4 Å molecular sieves
  0.5 mL solvent Enzyme and molecular sieves were added to the reaction vial first, followed by 0.5 mL of a stock solution of Ingenol and acyl donor in reaction solvent.

Screening reactions were shaken at room temperature for varying periods of time and then analysed by TLC (eluent 1:1 EtOAc/heptane, visualized by ceric sulfate stain and heating). Any reactions exhibiting formation of acylated product(s) were analysed by HPLC (Method A).

HPLC samples were prepared by adding 100 μL of reaction mixture to a glass pipette containing a cotton wool plug and washing through with ~1 mL of a 8:2 mixture of 25 mM $KH_2PO_4$ buffer (pH 2.2)/acetonitrile.

Due to the overlapping angelic anhydride peak, it was not possible to accurately quantify the level of PEP025 formation, but an approximate level could usually be obtained by peak splitting. Percentage conversions were calculated by taking into account relative response factors (RRFs) of Ingenol and PEP025 (see above).

A summary of the results is shown in Table 4.

TABLE 4

Summary of results for screening reactions with angelic anhydride in acetonitrile.

| | HLPC ANALYSIS (% conversion) | | | |
|---|---|---|---|---|
| ENZYME | PEP005 | PEP015 | PEP025 | Cmpd 4 |
| 01 | 0 | 0 | 25.6 | 0 |
| 03 | 1.4 | 0 | 29.1 | 0 |
| 04 | 0 | 0 | 94.6 | 0 |
| 10 | 0.3 | 0 | 45.8 | 0 |
| 17 | 4.8 | 0 | 0 | 0 |
| 32 | 0.7 | 0 | 0 | 0 |
| 33 | 0.9 | 0 | 0 | 0 |
| 36 | 1.1 | 0 | 0 | 0 |
| 37 | 0.5 | 0 | 0 | 0 |
| 39 | 0 | 0 | 55.1 | 0 |

TABLE 4-continued

Summary of results for screening reactions with
angelic anhydride in acetonitrile.

| | HLPC ANALYSIS (% conversion) | | | |
|---|---|---|---|---|
| ENZYME | PEP005 | PEP015 | PEP025 | Cmpd 4 |
| 40 | 0 | 0 | Not detectable | 0 |
| 44 | 0 | 0 | 4.0 | 0 |
| 48 | 2.0 | 0 | 0 | 0 |
| 49 | 0.5 | 0 | 24.0 | 0 |
| 50 | 0 | 0 | 10.5 | 0 |
| 51 | 0 | 0 | 4.0 | 0 |
| 54 | 2.0 | 0 | 0 | 0 |
| 55 | 0.6 | 0 | 26.1 | 0 |
| 57 | 0 | 0 | 81.7 | 0 |
| 58 | 0 | 0 | 21.5 | 0 |

The reactions were repeated at a variety of temperatures, at 6° C. (stirred in a fridge), 20° C. (shaken at room temperature), 30° C. (heated shaker) and 40° C. (shaken in an oven set to 40° C.). Reactions were shaken/stirred for 40 hours, then analysed by HPLC. A summary of the results is shown in Table 5.

TABLE 5

Summary of HPLC analysis for temperature experiments
with 17, 32, 33, 36, 37, 48 and 54.

| | | CONVERSION (%) | | | |
|---|---|---|---|---|---|
| ENZYME | TEMP (° C.) | PEP005 | PEP015 | PEP025 | Cmpd 4 |
| 17 | 6 | 0 | 0 | 0 | 0 |
| | 20 | 1.34 | 0 | 0 | 0 |
| | 30 | 0.95 | 0 | 0 | 0 |
| | 40 | 0.32 | 0 | 0 | 0 |
| 32 | 6 | 0 | 0 | 0 | 0 |
| | 20 | 0.48 | 0 | 0 | 0 |
| | 30 | 1.48 | 0 | 0 | 0 |
| | 40 | 0.71 | 0 | 0 | 0 |
| 33 | 6 | 0 | 0 | 0 | 0 |
| | 20 | 1.45 | 0 | 0 | 0 |
| | 30 | 1.79 | 0 | 0 | 0 |
| | 40 | 0.84 | 0 | 0 | 0 |
| 36 | 6 | 0 | 0 | 0 | 0 |
| | 20 | 0.42 | 0 | 0 | 0 |
| | 30 | 0.49 | 0 | 0 | 0 |
| | 40 | 0.98 | 0 | 0 | 0 |
| 37 | 6 | 0 | 0 | 0 | 0 |
| | 20 | 0.66 | 0 | 0 | 0 |
| | 30 | 1.12 | 0 | 0 | 0 |
| | 40 | 0.70 | 0 | 0 | 0 |
| 48 | 6 | 0 | 0 | 0 | 0 |
| | 20 | 0.93 | 0 | 0 | 0 |
| | 30 | 0.39 | 0 | 0 | 0 |
| | 40 | 0.30 | 0 | 0 | 0 |
| 54 | 6 | 0.7 | 0 | 0 | 0 |
| | 20 | 1.56 | 0 | 0 | 0 |
| | 30 | 2.91 | 0 | 0 | 0 |
| | 40 | 7.13 | 0.84 | 0 | 0.56 |

Surfactant Screening

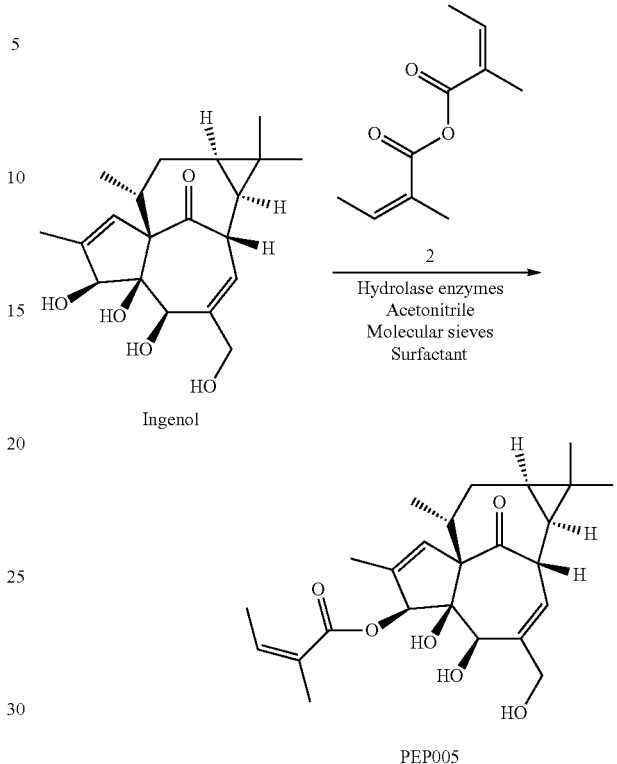

Surfactants are compounds that can influence the microenvironment of an enzyme, enhancing its activity and selectivity (Zheng, L. et al., Biocatalysis & Biotransformation, November-December 2007, 25(6), 430-433.)

Therefore the effect of a number of surfactants, the anionic surfactant dioctyl sodium sulfosuccinate (AOT), cationic surfactant cetyl trimethylammonium bromide (CTAB) and non-ionic polysorbate surfactant Tween-20, on the activity of hydrolases 17, 32, 33, 36, 37, 48 and 54 was investigated.

Standard screening conditions were employed with angelic anhydride as acyl donor and acetonitrile as reaction solvent, and with either 2.5% or 5% (w/v) surfactant. Reactions were shaken at room temperature for ~40 hours, then analysed by HPLC. These results are summarized in Table 6.

TABLE 6

Summary of HPLC analysis for surfactant experiments
with 17, 32, 33, 36, 37, 48 and 54.

| | SUR- | | CONVERSION (%) | | | |
|---|---|---|---|---|---|---|
| ENZYME | FACTANT | % (w/v) | PEP005 | PEP015 | PEP025 | Cmpd 4 |
| 17 | NONE | — | 1.34 | 0 | 0 | 0 |
| | AOT | 2.5 | 0 | 0 | 0 | 0 |
| | | 5 | 0.25 | 0 | 0 | 0 |
| | CTAB | 2.5 | 0 | 0 | 0 | 0 |
| | | 5 | 0.35 | 0 | 0 | 0 |
| | TWEEN-20 | 2.5 | 0.58 | 0 | 0 | 0 |
| | | 5 | 0.40 | 0 | 0 | 0 |
| 32 | NONE | — | 0.48 | 0 | 0 | 0 |
| | AOT | 2.5 | 0 | 0 | 0 | 0 |
| | | 5 | 0.31 | 0 | 0 | 0 |
| | CTAB | 2.5 | 1.58 | 0 | 0 | 0 |
| | | 5 | 1.25 | 0 | 0 | 0 |

TABLE 6-continued

Summary of HPLC analysis for surfactant experiments with 17, 32, 33, 36, 37, 48 and 54.

| ENZYME | SUR-FACTANT | % (w/v) | PEP005 | PEP015 | PEP025 | Cmpd 4 |
|---|---|---|---|---|---|---|
| | TWEEN-20 | 2.5 | 0.53 | 0 | 0 | 0 |
| | | 5 | 0.72 | 0 | 0 | 0 |
| 33 | NONE | — | 1.45 | 0 | 0 | 0 |
| | AOT | 2.5 | 0.46 | 0 | 0 | 0 |
| | | 5 | 1.03 | 0 | 0 | 0 |
| | CTAB | 2.5 | 0.73 | 0 | 0 | 0 |
| | | 5 | 0.84 | 0 | 0 | 0 |
| | TWEEN-20 | 2.5 | 0.44 | 0 | 0 | 0 |
| | | 5 | 0.37 | 0 | 0 | 0 |
| 36 | NONE | — | 0.42 | 0 | 0 | 0 |
| | AOT | 2.5 | 0 | 0 | 0 | 0 |
| | | 5 | 0.31 | 0 | 0 | 0 |
| | CTAB | 2.5 | 1.53 | 0 | 0 | 0 |
| | | 5 | 2.10 | 0 | 0 | 0 |
| | TWEEN-20 | 2.5 | 0.43 | 0 | 0 | 0 |
| | | 5 | 0.35 | 0 | 0 | 0 |
| 37 | NONE | — | 0.66 | 0 | 0 | 0 |
| | AOT | 2.5 | 0 | 0 | 0 | 0 |
| | | 5 | 0.29 | 0 | 0 | 0 |
| | CTAB | 2.5 | 0.73 | 0 | 0 | 0 |
| | | 5 | 0.68 | 0 | 0 | 0 |
| | TWEEN-20 | 2.5 | 0.44 | 0 | 0 | 0 |
| | | 5 | 0.54 | 0 | 0 | 0 |
| 48 | NONE | — | 0.93 | 0 | 0 | 0 |
| | AOT | 2.5 | 0 | 0 | 0 | 0 |
| | | 5 | 0.30 | 0 | 0 | 0 |
| | CTAB | 2.5 | 0.37 | 0 | 0 | 0 |
| | | 5 | 0.35 | 0 | 0 | 0 |
| | TWEEN-20 | 2.5 | 0.62 | 0 | 0 | 0 |
| | | 5 | 0.44 | 0 | 0 | 0 |
| 54 | NONE | — | 1.56 | 0 | 0 | 0 |
| | AOT | 2.5 | 0.90 | 0 | 0 | 0 |
| | | 5 | 0.92 | 0 | 0 | 0 |
| | CTAB | 2.5 | 14.5 | 2.0 | 5.1 | 2.7 |
| | | 5 | 13.0 | 2.1 | 4.1 | 1.7 |
| | TWEEN-20 | 2.5 | 0.83 | 0 | 0 | 0 |
| | | 5 | 0.72 | 0 | 0 | 0 |

Further Investigation of the Effect of CTAB on 54 Activity

Further experiments were carried out to investigate the effect of CTAB on the activity of 54. Reactions were shaken or stirred at different temperatures (20° C., 30° C., 40° C. and 50° C.) and with two concentrations of CTAB (1% and 2.5% (w/v)) for ~40 hours, then analysed by HPLC.

These results are summarized in Table 7,

TABLE 7

Summary of HPLC analysis for temperature experiments with 54 in the presence of CTAB.

| % CTAB (w/v) | TEMP (° C.) | PEP005 | PEP015 | PEP025 | Cmpd 4 | Cmpd 5 |
|---|---|---|---|---|---|---|
| 1 | 20 | 14.94 | 2.28 | 3.86 | 3.02 | 0 |
| | 30 | 24.56 | 5.60 | 9.49 | 11.22 | 1.46 |
| | 40 | 25.54 | 6.11 | 10.89 | 15.54 | 3.04 |
| | 50 | 23.04 | 5.32 | 13.27 | 25.38 | 8.61 |
| 2.5 | 20 | 14.49 | 2.03 | 5.14 | 2.74 | 0 |
| | 30 | 28.06 | 5.83 | 8.85 | 20.46 | 2.79 |
| | 40 | 27.96 | 5.98 | 8.49 | 26.47 | 5.21 |
| | 50 | 21.96 | 4.30 | 10.37 | 35.65 | 11.84 |

Formation of Diacylated Product and Ingenol-3-Angelate:

This reaction tested seven enzymes in a range of other solvents to see if any of them exhibited the selective formation of desired compound ingenol-3-angelate or secondary target ingenol-3,20-diangelate (compound 4). These solvents were:

Hexane
Heptane
Acetone
Toluene
Dichloromethane
DMF
THF
Diisopropyl ether
n-Butanol Each screening reaction contained:
2 mg Ingenol
1.5 eq. angelic anhydride 2 (1.57 mg)
1 small scoop of enzyme (~10 mg)
2 or 3 pellets of 4 Å molecular sieves
0.5 mL solvent Due to the insolubility of Ingenol in hexane, heptane and toluene, the substrate had to be measured into each individual reaction vial, whereas it was added as a stock solution for all other solvents.

Reactions were shaken at 28° C. for 88 hours (for solvents 1-4) or 69 hours (for solvents 5-9), then analysed by TLC (eluent 1:1 EtOAc/heptane, visualized by phosphomolybdic acid stain and heating) Acylated product spots were observed for the reactions in hexane, heptane, toluene, dichloromethane and diisopropyl ether.

The reactions in hexane, heptane, toluene, dichloromethane and diisopropyl ether were analysed by HPLC.

HPLC Samples were Prepared by the Following Procedure:

Reaction vials were left open in a well-ventilated fume hood overnight, or blown with a directed stream of nitrogen, to allow reaction solvent to evaporate. DMSO (150 µL) was then added to the residue to dissolve acylated product(s) and any remaining starting material. A 1:1 mixture of 25 mM $KH_2PO_4$ buffer (pH 2.2)/acetonitrile (~1 mL) was then added to dilute, and this was mixed before being filtered through a pipette containing a cotton wool plug into an HPLC vial for analysis. This was to ensure that the HPLC trace would accurately show the levels of the different reaction components, as heterogeneity of reaction mixtures ruled out accurate sampling.

These results are summarized in Table 8.

TABLE 8

Summary of solvent screening reactions with Ingenol and angelic anhydride 2 (1.5 eq).

| SOLVENT | ENZYME | HLPC ANALYSIS (% conversion) | | | |
|---|---|---|---|---|---|
| | | ingenol-3-angelate | PEP015 | PEP025 | Cmpd 4 |
| Hexane | 17 | 0.62 | 0.04 | 12.55 | 3.06 |
| | 32 | 0.30 | 0.04 | 9.56 | 2.41 |
| | 33 | 0.22 | 0.04 | 5.74 | 1.34 |
| | 36 | 0.52 | 0.03 | 21.94 | 5.03 |
| | 37 | 0.27 | 0.02 | 11.82 | 2.81 |
| | 48 | 0.24 | 0.05 | 6.36 | 1.52 |
| | 54 | 0.56 | 0.01 | 14.38 | 1.41 |
| Heptane | 17 | 0.61 | 0.04 | 10.53 | 2.39 |
| | 32 | 1.00 | 0.08 | 25.69 | 13.36 |
| | 33 | 0.64 | 0.03 | 10.46 | 3.65 |
| | 36 | 0.85 | 0.04 | 21.10 | 6.23 |
| | 37 | 0.71 | 0 | 18.31 | 12.42 |
| | 48 | 1.00 | 0.07 | 17.86 | 9.66 |
| | 54 | 0.77 | 0 | 17.23 | 2.76 |

TABLE 8-continued

Summary of solvent screening reactions with Ingenol and angelic anhydride 2 (1.5 eq).

| | | HLPC ANALYSIS (% conversion) | | | |
|---|---|---|---|---|---|
| SOLVENT | ENZYME | ingenol-3-angelate | PEP015 | PEP025 | Cmpd 4 |
| Toluene | 17 | 3.76 | 0.20 | 34.10 | 8.62 |
| | 32 | 4.83 | 0.25 | 34.53 | 13.30 |
| | 33 | 3.96 | 0.34 | 38.15 | 14.81 |
| | 36 | 2.82 | 0.15 | 39.36 | 12.57 |
| | 37 | 2.63 | 0.17 | 36.20 | 12.69 |
| | 48 | 2.16 | 0.38 | 38.56 | 25.03 |
| | 54 | 1.93 | 0 | 27.58 | 1.93 |
| DCM | 17 | 0.21 | 0 | 4.04 | 0 |
| | 32 | 0.80 | 0 | 10.67 | 0.42 |
| | 33 | 1.13 | 0 | 10.19 | 0.53 |
| | 36 | 1.49 | 0 | 14.40 | 0.65 |
| | 37 | 0.66 | 0 | 8.77 | 0.19 |
| | 48 | 0.76 | 0 | 8.52 | 0.26 |
| | 54 | 1.52 | 0 | 4.56 | 0.84 |
| Diisopropyl-Ether | 17 | 1.42 | 0.27 | 6.99 | 1.91 |
| | 32 | 0.49 | 0.17 | 2.85 | 0.88 |
| | 33 | 1.75 | 0.27 | 8.38 | 2.41 |
| | 36 | 2.21 | 0.38 | 17.78 | 4.72 |
| | 37 | 1.16 | 0.31 | 11.23 | 4.12 |
| | 48 | 1.28 | 0.44 | 6.97 | 2.89 |
| | 54 | 0.62 | 0 | 22.81 | 0.21 |

Investigation of Acyl Donor Equivalents

The following test reactions were run with the six enzymes listed above in hexane and heptane under the same conditions as given above, but in the presence of 2.5 equivalents of acyl donor. The results were compared to those obtained with 1.5 equivalents of acyl donor.

HPLC samples were prepared in the same manner as described above.

TABLE 9

Summary of screening reactions with Ingenol in hexane and heptane with 1.5 and 2.5 equivalents of angelic anhydride 2.

| | | | HPLC ANALYSIS (% conversion) | | | |
|---|---|---|---|---|---|---|
| SOLVENT | ENZYME | ACYL DONOR EQUIVALENTS | ingenol-3-angelate | PEP015 | PEP025 | Cmpd 4 |
| hexane | 17 | 1.5 | 0.62 | 0.04 | 12.55 | 3.06 |
| | | 2.5 | 0.06 | 0 | 4.17 | 0.91 |
| | 32 | 1.5 | 0.30 | 0.04 | 9.56 | 2.41 |
| | | 2.5 | 0.61 | 0.10 | 21.21 | 7.38 |
| | 33 | 1.5 | 0.22 | 0.04 | 5.74 | 1.34 |
| | | 2.5 | 0.33 | 0 | 8.93 | 2.46 |
| | 36 | 1.5 | 0.52 | 0.03 | 21.94 | 5.03 |
| | | 2.5 | 0.66 | 0 | 28.63 | 8.08 |
| | 37 | 1.5 | 0.27 | 0.02 | 11.82 | 2.81 |
| | | 2.5 | 0.42 | 0 | 23.56 | 7.88 |
| | 48 | 1.5 | 0.24 | 0.05 | 6.36 | 1.52 |
| | | 2.5 | 0.35 | 0.06 | 18.73 | 5.26 |
| heptane | 17 | 1.5 | 0.61 | 0.04 | 10.53 | 2.39 |
| | | 2.5 | 1.34 | 0.22 | 26.98 | 12.78 |
| | 32 | 1.5 | 1.00 | 0.08 | 25.69 | 13.36 |
| | | 2.5 | 1.43 | 0.20 | 36.69 | 24.40 |
| | 33 | 1.5 | 0.64 | 0.03 | 10.46 | 3.65 |
| | | 2.5 | 1.35 | 0.24 | 23.29 | 12.48 |
| | 36 | 1.5 | 0.85 | 0.04 | 21.10 | 6.23 |
| | | 2.5 | 1.31 | 0.13 | 27.13 | 12.21 |
| | 37 | 1.5 | 0.71 | 0 | 18.31 | 12.42 |
| | | 2.5 | 0.75 | 0.20 | 43.58 | 33.88 |
| | 48 | 1.5 | 1.00 | 0.07 | 17.86 | 9.66 |
| | | 2.5 | 1.49 | 0.08 | 26.57 | 14.86 |

Extended Solvent Screening

The initial sets of expanded solvent screening reactions were carried out with enzymes 17, 32, 33, 36, 37, 48 and 54.

Conditions were the same as for the reactions above (2.5 equivalents of acyl donor). Three reaction solvents were investigated—hexane, heptane and toluene.

HPLC samples were prepared in the same manner as described above.

Screening Reactions in Hexane

Reactions were shaken at 30° C. for 89 hours then analysed by HPLC. The results are summarized in Table 10.

TABLE 10

Summary of screening reactions with Ingenol in hexane with 2.5 equivalents of angelic anhydride 2.

| | HLPC ANALYSIS (% conversion) | | | |
|---|---|---|---|---|
| ENZYME | ingenol-3-angelate | PEP015 | PEP025 | Cmpd 4 |
| 01 | 0.21 | 0 | 49.20 | 41.20 |
| 02 | 0.76 | 0 | 41.38 | 9.25 |
| 03 | 0.15 | 0 | 74.08 | 25.77 |
| 04 | 0.15 | 0 | 93.78 | 5.10 |
| 05 | 0.81 | 0 | 33.53 | 7.52 |
| 06 | 0.29 | 0 | 35.55 | 1.57 |
| 07 | 0.65 | 0.10 | 39.55 | 8.96 |
| 08 | 0.03 | 0 | 67.89 | 31.25 |
| 09 | 0.71 | 0 | 40.42 | 4.20 |
| 10 | 0 | 0.01 | 86.45 | 13.54 |
| 17 | 0.06 | 0 | 4.17 | 0.91 |
| 24 | 0.33 | 0 | 42.40 | 2.02 |
| 32 | 0.61 | 0.10 | 21.21 | 7.38 |
| 33 | 0.33 | 0 | 8.93 | 2.46 |
| 35 | 1.10 | 0 | 41.39 | 5.76 |
| 36 | 0.66 | 0 | 28.63 | 8.08 |

TABLE 10-continued

Summary of screening reactions with Ingenol in hexane with 2.5 equivalents of angelic anhydride 2.

| | HLPC ANALYSIS (% conversion) | | | |
|---|---|---|---|---|
| EN-ZYME | ingenol-3-angelate | PEP015 | PEP025 | Cmpd 4 |
| 37 | 0.42 | 0 | 23.56 | 7.88 |
| 39 | 0.02 | 0 | 98.02 | 1.96 |
| 40 | 0 | 0 | 22.36 | 0 |
| 41 | 0 | 0 | 0 | 0 |
| 44 | 0 | 0 | 0 | 0 |
| 48 | 0.35 | 0.06 | 18.73 | 5.26 |
| 49 | 0.13 | 0 | 95.96 | 2.58 |
| 50 | 0.09 | 0 | 2.18 | 0.13 |
| 51 | 0 | 0 | 0.99 | 0 |
| 53 | 0 | 0 | 0.71 | 0 |
| 55 | 0 | 0 | 1.73 | 0 |
| 57 | 0.33 | 0.04 | 8.32 | 0.67 |
| 58 | 0.20 | 0 | 2.66 | 0.07 |

Screening Reactions in Heptane

Reactions were shaken at 30° C. for 93 hours then analysed by HPLC. The results are summarized in Table 11.

TABLE 11

Summary of screening reactions with Ingenol in heptane with 2.5 equivalents of angelic anhydride 2.

| | HLPC ANALYSIS (% conversion) | | | |
|---|---|---|---|---|
| EN-ZYME | ingenol-3-angelate | PEP015 | PEP025 | Cmpd 4 |
| 01 | 0.57 | 0 | 40.26 | 26.27 |
| 02 | 0 | 0 | 42.63 | 22.40 |
| 03 | 0 | 0 | 65.71 | 34.29 |
| 04 | 0 | 0 | 87.25 | 6.32 |
| 05 | 0 | 0 | 47.70 | 22.99 |
| 06 | 0.33 | 0 | 47.99 | 4.94 |
| 07 | 0.53 | 0 | 35.93 | 12.93 |
| 08 | 0 | 0 | 63.39 | 36.61 |
| 09 | 0.70 | 0 | 55.27 | 13.35 |
| 10 | 0.38 | 0 | 67.52 | 7.26 |
| 17 | 1.34 | 0.22 | 26.98 | 12.78 |
| 24 | 0.30 | 0 | 46.78 | 28.14 |
| 32 | 1.43 | 0.20 | 36.69 | 24.40 |
| 33 | 1.35 | 0.24 | 23.29 | 12.48 |
| 35 | 1.38 | 0 | 41.82 | 12.31 |
| 36 | 1.31 | 0.13 | 27.13 | 12.21 |
| 37 | 0.75 | 0.20 | 43.58 | 33.88 |
| 39 | 0 | 0 | 57.61 | 0 |
| 40 | 0 | 0 | 53.71 | 0 |
| 41 | 0 | 0 | 0 | 0 |
| 44 | 0 | 0 | 0 | 0 |
| 48 | 1.49 | 0.08 | 26.57 | 14.86 |
| 49 | 0.58 | 0 | 86.63 | 4.90 |
| 50 | 0.13 | 0 | 3.51 | 0 |
| 51 | 0 | 0 | 0.83 | 0 |
| 53 | 0 | 0 | 0 | 0 |
| 55 | 0.05 | 0 | 2.16 | 0 |
| 57 | 0 | 0 | 10.08 | 1.43 |
| 58 | 0 | 0 | 5.02 | 0.14 |

Screening Reactions in Toluene

The reactions were shaken at 30° C. for 70 hours then analysed by HPLC. The results are summarized in Table 12.

TABLE 12

Summary of screening reactions with Ingenol in toluene with 2.5 equivalents of angelic anhydride 2.

| | HPLC ANALYSIS (% conversion) | | | |
|---|---|---|---|---|
| ENZYME | ingenol-3-angelate | PEP015 | PEP025 | Cmpd 4 |
| 01 | 2.15 | 0 | 45.39 | 10.63 |
| 02 | 1.84 | 0 | 50.82 | 5.23 |
| 03 | 1.56 | 0.01 | 64.11 | 11.95 |
| 04 | 0.13 | 0 | 94.74 | 5.13 |
| 05 | 1.31 | 0 | 62.60 | 6.42 |
| 06 | 0.11 | 0 | 91.73 | 0.58 |
| 07 | 1.65 | 0 | 33.48 | 1.54 |
| 08 | 0 | 0 | 94.38 | 4.11 |
| 09 | 0.78 | 0 | 77.17 | 1.12 |
| 10 | 0.79 | 0 | 87.96 | 7.78 |
| 17 | 3.45 | 0 | 30.79 | 6.41 |
| 24 | 2.28 | 0 | 51.35 | 4.11 |
| 32 | 2.77 | 0 | 34.52 | 6.35 |
| 33 | 2.69 | 0 | 26.08 | 4.41 |
| 35 | 1.87 | 0 | 51.68 | 5.62 |
| 36 | 2.65 | 0 | 30.62 | 3.86 |
| 37 | 4.85 | 0 | 35.87 | 10.92 |
| 48 | 2.95 | 0 | 39.02 | 8.51 |

Further Acylation Screening in Heptane

A number of parameters were investigated simultaneously—the effect of higher temperature (running reactions at 30° C. and 50° C.), the effect of higher equivalents of acyl donor 2 (running reactions with either 2.5 or 4 equivalents), and the effect of the presence of triethylamine. Experiments were carried out with hydrolases 01, 03 and 08.

Two sets of reactions were carried out—set 1 at 30° C., and set 2 at 50° C. Reactions contained the following:

2 mg Ingenol 2.5 eq. (2.62 mg) or 4 eq. (4.18 mg) angelic anhydride 2

1 small scoop of enzyme 2 or 3 pellets of 4 Å molecular sieves 0.5 mL heptane

Each reaction was carried out in duplicate—one in the presence of triethylamine (either 2.5 or 4 equivalents, depending on the equivalents of angelic anhydride 2), and one in the absence of triethylamine.

Due to the insolubility of Ingenol in heptane, the substrate was measured into each individual reaction vial. This was followed by the addition of enzyme and molecular sieves, then a solution of angelic anhydride 2 in heptane (containing triethylamine where appropriate). Reactions were shaken at 30° C. or 50° C. for 64 hours, then analysed by HPLC (procedure for the preparation of HPLC samples is given in Section 9.1).

The results are summarized in Table 13.

TABLE 13

Summary of screening reactions with Ingenol in heptane, varying temperature, equivalents of acyl donor, and the presence of triethylamine.

| ENZYME | TEMP (° C.) | ACYL DONOR EQUIVALENTS | ET$_3$N | ingenol-3-angelate | PEP015 | PEP025 | Cmpd 4 |
|---|---|---|---|---|---|---|---|
| 01 | 30 | 2.5 | YES | 0.36 | 0 | 72.45 | 18.05 |
|  |  |  | NO | 0.33 | 0 | 53.96 | 24.53 |
|  |  | 4 | YES | 0.09 | 0 | 48.73 | 51.17 |
|  |  |  | NO | 0 | 0 | 56.11 | 36.35 |
|  | 50 | 2.5 | YES | 0 | 0 | 56.49 | 43.51 |
|  |  |  | NO | 0 | 0 | 51.94 | 48.06 |
|  |  | 4 | YES | 0 | 0 | 22.94 | 77.06 |
|  |  |  | NO | 0 | 0 | 26.89 | 73.11 |
| 03 | 30 | 2.5 | YES | 0 | 0 | 75.15 | 22.84 |
|  |  |  | NO | 0.04 | 0 | 77.22 | 21.68 |
|  |  | 4 | YES | 0.04 | 0 | 61.61 | 38.35 |
|  |  |  | NO | 0.03 | 0 | 58.17 | 41.80 |
|  | 50 | 2.5 | YES | 0 | 0 | 55.29 | 44.71 |
|  |  |  | NO | 0 | 0 | 56.28 | 43.72 |
|  |  | 4 | YES | 0 | 0 | 36.32 | 63.68 |
|  |  |  | NO | 0 | 0 | 39.13 | 60.87 |
| 08 | 30 | 2.5 | YES | 0.05 | 0 | 78.04 | 21.91 |
|  |  |  | NO | 0.05 | 0 | 75.66 | 23.20 |
|  |  | 4 | YES | 0 | 0 | 67.21 | 28.35 |
|  |  |  | NO | 0 | 0 | 58.64 | 40.84 |
|  | 50 | 2.5 | YES | 0.08 | 0 | 81.85 | 18.08 |
|  |  |  | NO | 0 | 0 | 84.12 | 15.88 |
|  |  | 4 | YES | 0 | 0 | 47.17 | 52.83 |
|  |  |  | NO | 0.06 | 0 | 30.83 | 69.12 |

Investigating the Effect of Surfactants on Enzyme Activity

The effect of surfactants on the eight enzymes in heptane—01, 02, 03, 05, 08, 24, 32 and 37 were tested. Three surfactants were chosen—the anionic surfactant dioctyl sodium sulfosuccinate (AOT), cationic surfactant CTAB and non-ionic polysorbate surfactant Tween-20.

The enzyme was pre-treated with a solution of surfactant and freeze-dried.

Freeze-dried surfactant-coated hydrolase enzymes were prepared as follows:

AOT & CTAB:

1.8 g of surfactant was added to 72 mL distilled H$_2$O (2.5% w/v). This was stirred and sonicated to dissolve. Complete dissolution did not occur due to poor solubility of these compounds in water. The solution was separated from the undissolved surfactant and used for enzyme treatment by adding 3 mL to 50 mg of each hydrolase. This was then freeze-dried overnight.

Tween-20:

1.8 g of surfactant was dissolved in 18 mL H$_2$O (10% w/v), and 1.5 mL of this solution was added to 100 mg of each hydrolase. This was then freeze-dried overnight.

Hydrolases 24, 32 and 37 did not freeze-dry properly with Tween-20 (probably due to the high viscosity of this surfactant). Therefore a drop of Tween-20 was simply added to reactions with these enzymes.

Each reaction contained the following:
2 mg Ingenol
2.5 eq. angelic anhydride 2 (2.62 mg)
1-3 scoops of enzyme (depending on the 'fluffiness' of treated enzyme)
2 or 3 pellets of 4 Å molecular sieves
0.5 mL heptane For each enzyme, an additional reaction was also carried out using untreated enzyme for comparison. Reactions were shaken at 30° C. for 65 hours, then analysed by HPLC (procedure for the preparation of HPLC samples is given in Section 9.1).

The results are summarized in Table 14.

TABLE 14

Summary of screening reactions on Ingenol with surfactant-treated hydrolases in heptane.

| ENZYME | SURFACTANT | ingenol-3-angelate | PEP015 | PEP025 | Cmpd 4 |
|---|---|---|---|---|---|
| 01 | AOT | 1.07 | — | 30.31 | 0.40 |
|  | CTAB | 0.61 | — | 9.63 | 1.14 |
|  | Tween-20 | 1.58 | — | 10.71 | 0.73 |
|  | None | 0.43 | — | 53.58 | 30.12 |
| 02 | AOT | 2.07 | — | 31.46 | 0.38 |
|  | CTAB | 0.75 | — | 4.09 | 0.93 |
|  | Tween-20 | 0.62 | — | 2.33 | 0 |
|  | None | 0.10 | — | 40.24 | 7.81 |
| 03 | AOT | 0 | — | 95.39 | 4.61 |
|  | CTAB | 0.86 | — | 15.21 | 3.02 |
|  | Tween-20 | 1.27 | — | 21.20 | 0 |
|  | None | 0 | — | 64.58 | 35.42 |
| 05 | AOT | 0 | — | 19.52 | 0.19 |
|  | CTAB | 0 | — | 6.53 | 0.95 |
|  | Tween-20 | 1.09 | — | 23.88 | 1.58 |
|  | None | 0 | — | 81.95 | 18.05 |
| 08 | AOT | 1.27 | — | 34.87 | 0.40 |
|  | CTAB | 0.59 | — | 22.79 | 1.14 |
|  | Tween-20 | 1.24 | — | 6.98 | 0.68 |
|  | None | 0 | — | 66.97 | 26.35 |
| 24 | AOT | 0 | — | 14.61 | 0.66 |
|  | CTAB | 0.29 | — | 2.58 | 0.29 |
|  | Tween-20 | 0 | — | 63.52 | 0.24 |
|  | None | 0.42 | — | 49.03 | 24.03 |
| 32 | AOT | 0.99 | — | 10.60 | 0.30 |
|  | CTAB | 0.36 | — | 3.36 | 0.77 |
|  | Tween-20 | 1.10 | — | 0.79 | 0.09 |
|  | None | 0.13 | — | 6.52 | 1.62 |

TABLE 14-continued

Summary of screening reactions on Ingenol with surfactant-treated hydrolases in heptane.

| ENZYME | SURFACTANT | HPLC ANALYSIS (% conversion) | | | |
|---|---|---|---|---|---|
| | | ingenol-3-angelate | PEP015 | PEP025 | Cmpd 4 |
| 37 | AOT | 0 | — | 19.12 | 0.25 |
| | CTAB | 0.61 | — | 11.12 | 0.91 |
| | Tween-20 | 0 | — | 0 | 0 |
| | None | 0.71 | — | 19.67 | 7.99 |

Further optimization of the above reaction was investigated:

An initial set of experiments was carried out using the eight previously identified lead enzymes in order to narrow the choice to two enzymes for further study. Reactions were carried out at a significantly higher substrate concentration than previously investigated (20 mg/reaction instead of 2 mg/reaction), and enzyme loading was accurately measured to 10 mg (50% w/w with respect to substrate loading).

Reactions were carried out in HPLC vials and contained the following:
20 mg Ingenol
2.5 eq. angelic anhydride 2 (26.2 mg)
10 mg enzyme (50% w/w with respect to substrate)
2 or 3 pellets of 4 Å molecular sieves
0.5 mL heptane Enzyme, Ingenol and molecular sieves were added to the reaction vial first, followed by 0.5 mL of a solution of angelic anhydride 2 in heptane. Reactions were shaken at 50° C. for 70 hours, then analysed by TLC for evidence of compound 4 formation. This was clearly seen for all eight enzymes.

Reactions were worked up by evaporating the heptane solvent with a directed stream of nitrogen gas. The residue was then dissolved in dichloromethane to ensure that all reaction components were in solution. A 20 µL sample was taken from each and added to an HPLC vial, where the solvent was evaporated with a directed stream of nitrogen and the residue re-dissolved in a 1:1 mixture of 25 mM $KH_2PO_4$ (pH 2.2)/acetonitrile and analysed by HPLC (Table 14). In addition to Ingenol, PEP025 and compound 4, a number of minor peaks exhibiting the characteristic UV absorption for Ingenol were observed. These side-products were relatively consistent across all eight reactions, and for expediency were therefore not taken into account when calculating conversions to PEP025 and compound 4. These reactions were simply for the purpose of identifying the two most promising lead enzymes for further investigation.

Out of the eight enzymes, three (AH-03, AH-05 and AH-08) exhibited total consumption of Ingenol starting material, as well as the highest proportion of compound 4 formation. The two lead enzymes chosen for further study were AH-03 and AH-08.

TABLE 14

Summary of experiment ALM2213209 results (highlighted reactions had no Ingenol remaining).

| ENZYME | HPLC ANALYSIS (% area)* | | | | |
|---|---|---|---|---|---|
| | Ingenol | PEP005 | PEP015 | PEP025 | Cmpd 4 |
| AH-01 | 9.88 | 0 | 0 | 45.33 | 44.79 |
| AH-02 | 6.72 | 0 | 0 | 46.15 | 47.13 |
| AH-03 | 0 | 0 | 0 | 33.50 | 66.50 |
| AH-05 | 0 | 0 | 0 | 38.70 | 61.30 |
| AH-08 | 0 | 0 | 0 | 38.01 | 61.99 |
| AH-24 | 23.99 | 0 | 0 | 41.78 | 34.23 |
| AH-32 | 20.56 | 0 | 0 | 43.12 | 36.32 |
| AH-37 | 27.31 | 0 | 0 | 37.70 | 34.99 |

*Corrected for differences in UV response factor at 235 nm

1.1. Experiment ALM2213213

Substrate Loading at 60° C.

Further investigation was carried out with the two identified lead enzymes (AH-03 and AH-08) with different substrate loadings. The effect of the presence of 1.5 equivalents of triethylamine base was also examined, as it was thought that 'mopping up' the angelic acid formed could have resulted in higher reaction rates. Reactions were carried out at 60° C. to assess if this higher temperature could increase reaction rate without resulting in inactivation of enzyme and/or excessive side-product formation.

All reactions were carried out in 0.5 mL heptane containing 2.5 equivalents of angelic anhydride 2, 50% w/w enzyme, and 2-3 pellets of 4 Å molecular sieves. Four different reaction conditions were investigated for each enzyme:

Reaction A: 20 mg Ingenol, 26.1 mg angelic anhydride 2, 10 mg enzyme+1.5 eq $Et_3N$ (12 µL).

Reaction B: 20 mg Ingenol, 26.1 mg angelic anhydride 2, 10 mg enzyme.

Reaction C: 40 mg Ingenol, 52.3 mg angelic anhydride 2, 20 mg enzyme.

Reaction D: 60 mg Ingenol, 78.5 mg angelic anhydride 2, 30 mg enzyme.

Blank: 60 mg Ingenol, 78.5 mg angelic anhydride 2 (NO ENZYME).

Reactions were shaken at 60° C. and sampled at daily intervals for HPLC analysis. This served as an indication of the ratio of PEP025/compound 4 formation rather than an exact assessment of conversion due to the low solubility of Ingenol in heptane (both acylated products exhibit higher solubility in heptane). The desired diacylation was observed to occur for all reactions. Interestingly, the two reactions carried out in the presence of triethylamine base appeared to proceed the fastest, although this was accompanied by a higher level of undesired side-product formation. The same was observed with hydrolase AH-08.

By day 3, the rate of product formation was observed to have slowed significantly for all reactions, none of which showed complete disappearance of PEP025. It was considered possible that the high temperature (60° C.) may have resulted in gradual loss of enzyme activity. Therefore a further 50% w/w enzyme was added to each reaction (A-D) and shaking was continued for a further three days (over the weekend). After this point, the reactions were worked up (as described in Section 10.1) to get a representative sample

TABLE 15

Summary of experiment ALM2213213 final analysis results.

| | | HPLC ANALYSIS (% area)* | | | | | |
|---|---|---|---|---|---|---|---|
| ENZYME | CONDITIONS | Ingenol | PEP005 | PEP015 | PEP025 | Cmpd 4 | Others |
| AH-03 | A | 0 | 1.37 | 0 | 10.18 | 53.38 | 35.07 |
| | B | 0 | 0 | 0 | 14.16 | 62.61 | 23.23 |
| | C | 1.57 | 0.69 | 0 | 21.60 | 55.11 | 21.03 |
| | D | 1.06 | 0.80 | 0 | 23.45 | 52.17 | 22.52 |
| AH-08 | A | 0 | 1.74 | 0 | 7.71 | 54.63 | 35.92 |
| | B | 0 | 0.75 | 0 | 11.61 | 63.35 | 24.29 |
| | C | 1.25 | 1.72 | 0 | 21.19 | 54.96 | 20.88 |
| | D | 1.81 | 1.77 | 0 | 24.70 | 51.28 | 20.43 |
| — | BLANK | 0.52 | 0 | 0 | 15.88 | 57.76 | 25.84 | of all reaction components for HPLC analysis. These results are summarised in Table 15.
*Corrected for differences in UV response factor at 235 nm A number of side-products with the characteristic UV absorbance of Ingenol were observed to form. These were each assigned an estimated response factor of 1 to facilitate calculation of corrected % areas. As seen in Table 15, all reactions exhibited combined side-products of >20% (>35% for reactions in the presence of triethylamine). It was known that the Ingenol used for these reactions was not of high purity ($^1$H NMR assay gave a purity of 81.4%), therefore it is possible that some of these side-products may be due to the reaction of angelic anhydride with structurally-related impurities.

It was also observed that all enzyme-containing reactions exhibited complete consumption of angelic anhydride 2 after 6 days despite being present in excess, thereby preventing complete conversion of PEP025 to compound 4. By comparison, the blank reaction without enzyme still contained unreacted anhydride. This implies that the anhydride was also reacting with the enzyme itself (perhaps acylating various amino acid residues on the protein structure) or with excipients present in the enzyme formulation.

Interestingly, at the substrate concentration and temperature investigated, essentially complete consumption of Ingenol was observed in the absence of enzyme (blank reaction), with the accompanying formation of PEP025 and compound 4. This non-enzymatic acylation was not observed in previous screening experiments, which were carried out at significantly lower substrate concentration (2 mg/reaction) and temperature (30° C.). This non-enzymatic reaction retains the desired acylation selectivity and therefore warrants further investigation as enzyme may not be required at all.

It also worth noting that even though reaction D and the blank reaction both had the same substrate concentration (60 mg/reaction), the blank reaction proceeded to a higher proportion of compound 4. This is likely due to the aforementioned consumption of angelic anhydride 2 in the enzyme-containing reactions, preventing further acylation from occurring.

Check for Isomerisation of Angelate to Tiglate

Under certain conditions, angelate can isomerise to tiglate (FIGURE below). This isomerisation is undesired, and therefore it is important to check for the presence of tiglate in acylation/deacylation reactions.

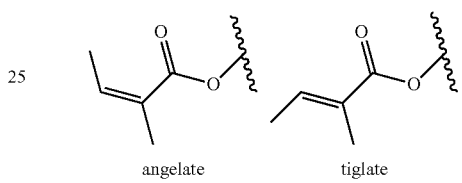

angelate        tiglate

The Structures of Angelate (Z-Isomer) and Tiglate (E-Isomer).

It was decided to carry out quick purifications on reaction D for both AH-03 and AH-08, as well as the blank reaction without enzyme, in order to isolate some of the synthesised compound 4 for $^1$H NMR analysis (as the crude NMR spectra were quite messy). In all three cases, compound 4 was isolated by silica chromatography (eluent gradient from 100% hexane to 85:15 hexane/EtOAc).

The $^1$H NMR spectrum of isolated compound 4 from reaction D with AH-03 is shown in FIG. 1. No undesired tiglate formation was observed (for which a characteristic signal ~6.9 ppm would be seen). This was the same for all three reactions.

Experiment ALM2232019

Substrate Loading at 30° C. & 50° C.

The conditions of experiment ALM2213213 were repeated, but at 30° C. and 50° C. This was to determine if higher temperature is necessary for the reaction to proceed satisfactorily, and also to see if a higher proportion of undesired side-products are observed at higher temperatures.

The reactions were sampled at daily intervals to check on reaction progress. After 6 days the reactions were worked up to get a homogeneous sample and analysed by HPLC. The results are shown in Table 15A (for reactions at 30° C.) and Table 16 (for reactions at 50° C.).

TABLE 15A

Summary of experiment ALM2232019 final analysis results (30° C.).

| | | HPLC ANALYSIS (% area)* | | | | | |
|---|---|---|---|---|---|---|---|
| ENZYME | CONDITIONS | Ingenol | PEP005 | PEP015 | PEP025 | Cmpd 4 | Others |
| AH-03 | A | 0 | 0 | 0 | 9.77 | 52.65 | 37.58 |
| | B | 8.15 | 0 | 0 | 42.56 | 37.39 | 11.90 |
| | C | 0.60 | 0.37 | 0 | 24.97 | 58.09 | 15.97 |
| | D | 0.13 | 0.16 | 0 | 34.54 | 46.82 | 13.35 |
| AH-08 | A | 0 | 0 | 0 | 10.58 | 54.69 | 34.72 |
| | B | 1.58 | 0 | 0 | 45.51 | 40.43 | 12.48 |
| | C | 1.04 | 0.24 | 0 | 36.58 | 46.98 | 15.17 |
| | D | 0.68 | 0 | 0 | 36.23 | 47.88 | 15.21 |
| — | BLANK | 24.53 | 2.70 | 0 | 31.96 | 32.86 | 7.96 |

*Corrected for differences in UV response factor at 235 nm

TABLE 16

Summary of experiment ALM2232019 final analysis results (50° C.). Once again, all reactions in the presence of triethylamine were observed to proceed the fastest, but with an unacceptably high proportion of undesired side-product formation.

| | | HPLC ANALYSIS (% area)* | | | | | |
|---|---|---|---|---|---|---|---|
| ENZYME | CONDITIONS | Ingenol | PEP005 | PEP015 | PEP025 | Cmpd 4 | Others |
| AH-03 | A | 0 | 0 | 0 | 2.56 | 53.63 | 43.81 |
| | B | 0 | 0 | 0 | 14.21 | 63.83 | 21.96 |
| | C | 0 | 0 | 0 | 18.82 | 55.61 | 25.58 |
| | D | 0 | 0 | 0 | 21.83 | 54.56 | 23.61 |
| AH-08 | A | 0 | 0 | 0 | 0.67 | 51.51 | 47.82 |
| | B | 0 | 0 | 0 | 8.00 | 63.64 | 28.35 |
| | C | 0 | 0 | 0 | 17.33 | 58.30 | 24.37 |
| | D | 0 | 0 | 0 | 25.82 | 51.65 | 22.53 |
| — | BLANK | 0 | 0 | 0 | 19.99 | 59.25 | 20.75 |

*Corrected for differences in UV response factor at 235 nm

Unsurprisingly, the reactions at 30° C. were observed to proceed more slowly than those at 50° C. or 60° C. No reactions had reached completion after 6 days. However, all enzyme-containing reactions proceeded further than the blank reaction, which still contained ~24% unreacted Ingenol. This implies that the non-enzymatic acylation proceeds better at higher temperatures. Indeed, after a certain temperature, the presence of enzyme may simply be unnecessary.

The reactions at 50° C. gave very similar results to those at 60° C. Once again, the blank reaction proceeded to a higher proportion of compound 4 than reaction D, despite having the same substrate concentration (60 mg/reaction). This is likely due to the aforementioned consumption of angelic anhydride 2 in the enzyme-containing reactions, preventing further acylation from occurring.

Experiment ALM2232023

Investigation of Non-Enzymatic Acylation

The results described above revealed that the acylation of Ingenol to form compound 4 (via PEP025) can occur in the absence of enzyme at elevated temperature. This warranted further investigation, as it may be possible to develop satisfactory non-enzymatic conditions for the synthesis of compound 4, thereby reducing the cost of materials required.

To further investigate this non-enzymatic acylation, a number of experiments were carried out at higher temperatures (70° C. and 80° C.). The effect of the presence of triethylamine was also investigated (as this was only previously examined for enzyme-containing reactions).

All reactions were carried out in 0.5 mL heptane containing 2.5 equivalents of angelic anhydride 2 and 2-3 pellets of 4 Å molecular sieves. Four different reaction conditions were investigated:
Reaction A: 60 mg Ingenol at 70° C.
Reaction B: 60 mg Ingenol+2 eq $Et_3N$ (48 µL) at 70° C.
Reaction C: 60 mg Ingenol at 80° C.
Reaction D: 60 mg Ingenol+2 eq $Et_3N$ (48 µL) at 80° C.

Reactions were magnetically stirred for ~65 hours, after which reactions B & D were observed to be dark brown compared to the pale yellow of reactions A & C. Initial TLC analysis revealed that reactions B & D had no PEP025 remaining, implying that full acylation to compound 4 had occurred (whereas PEP025 was observed for reactions A & C). Reactions were homogenised by the addition of dichloromethane (0.7 mL), and then sampled for HPLC analysis (Table 17). This revealed that reactions B & D did indeed have no PEP025 remaining, although a very large proportion of undesired and unidentified side-products (~70% area measured on HPLC) were formed. This unequivocally confirms that the presence of triethylamine is detrimental to the reaction.

TABLE 17

Summary of experiment ALM2232023 final analysis results.

| CONDITIONS | HPLC ANALYSIS (% area)* | | | | | |
|---|---|---|---|---|---|---|
| | Ingenol | PEP005 | PEP015 | PEP025 | Cmpd 4 | Others |
| A | 1.78 | 0 | 0 | 21.96 | 55.77 | 20.49 |
| B | 0 | 0 | 0 | 0.18 | 30.56 | 69.26 |
| C | 1.42 | 0 | 0 | 21.26 | 57.72 | 19.60 |
| D | 0 | 0 | 0 | 0 | 28.77 | 71.23 |

The ratio of PEP025 to compound 4 for reactions A & C was compared to that observed for the equivalent reactions at 30° C., 50° C. and 60° C. after approximately the same length of time (~64-72 hours) (Table 18). This clearly shows that the degree of non-enzymatic diacylation increases with temperature.

With additional reaction time, it may be possible to get complete conversion of PEP025 to compound 4.

TABLE 18

Comparison of the ratio of PEP025 to compound 4 for non-enzymatic acylation of Ingenol at 30° C., 50° C., 60° C. and 70° C. after ~64-72 hours.

| TEMPERATURE (° C.) | RATIO OF PEP025 TO COMPOUND 4 |
|---|---|
| 30 | 1:1.33 |
| 50 | 1:2.54 |
| 60 | 1:3.18 |
| 70 | 1:4.17 |
| 80 | 1:4.46 |

1.2. Experiment ALM2232027

Effect of Non-Nucleophilic Bases

It was decided to further investigate the non-enzymatic acylation of Ingenol by assessing the impact of the presence of various non-nucleophilic bases. It was hoped that one or more of these bases would be able to maximise the level of compound 4 formation without resulting in undesired isomerisation of angelate to tiglate. Five reactions were carried out:

A) $Cs_2CO_3$
B) $K_2CO_3$
C) $NaHCO_3$
D) $K_3PO_4$
E) No base (for comparison)

Reactions were carried out in HPLC vials and contained the following:

20 mg Ingenol
2.5 eq. angelic anhydride 2 (26.2 mg)
2 equivalents of base
2 or 3 pellets of 4 Å molecular sieves
0.5 mL heptane Reactions were shaken at 50° C. and sampled for HPLC analysis after ~18 hours to check on reaction progress. The desired diacylation was observed to occur for all reactions. The level of compound 4 was highest for reactions B and D. Reaction A also showed a high level of compound 4, but was accompanied by a higher percentage of undesired side-products. Reaction C was markedly slower than reactions A, B and D. Reactions A-D all proceeded further than reaction E without base.

The reactions were allowed to shake at 50° C. for a further 3 nights, then homogenised by the addition of dichloromethane (0.7 mL). A sample of each (~30 µL) was taken and evaporated with a directed stream of nitrogen, and the residue dissolved in a 1:1 mixture of 25 mM $KH_2PO_4$ (pH 2.2)/acetonitrile for HPLC analysis. The results are shown in Table 19.

TABLE 19

Summary of experiment ALM2232027 results.

| REACTION | BASE | HPLC ANALYSIS (% area) | | | | | |
|---|---|---|---|---|---|---|---|
| | | Ingenol | PEP005 | PEP015 | PEP025 | Cmpd 4 | Others |
| A | $Cs_2CO_3$ | 3.52 | 0.55 | 0 | 10.45 | 55.75 | 29.73 |
| B | $K_2CO_3$ | 0 | 0 | 0 | 4.99 | 72.45 | 22.56 |
| C | $NaHCO_3$ | 0 | 0 | 0 | 17.12 | 61.04 | 21.85 |
| D | $K_3PO_4$ | 0 | 0 | 0 | 7.38 | 70.20 | 22.42 |
| E | — | 3.16 | 0 | 0 | 34.78 | 48.61 | 13.44 |

It is clear that the presence of base improved the level of conversion to compound 4, particularly with $K_2CO_3$ and $K_3PO_4$. $^1$H NMR analysis of each crude reaction showed that no detectable isomerisation of angelate to tiglate had occurred.

To see if the reaction could be pushed to completion (i.e. all PEP025 intermediate converted to compound 4), the reactions with $K_2CO_3$ and $K_3PO_4$ were repeated, but with larger amounts of base and anhydride (2.4 and 3 equivalents, respectively). After only one night, both reactions were almost complete. After two nights, both reactions were worked up and analysed by HPLC (Table 20).

TABLE 20

Summary of experiment ALM2232027 results with larger amounts of angelic anhydride and $K_2CO_3$ or $K_3PO_4$.

| REACTION | BASE | HPLC ANALYSIS (% area) | | | | | |
|---|---|---|---|---|---|---|---|
| | | Ingenol | PEP005 | PEP015 | PEP025 | Cmpd 4 | Others |
| F | $K_2CO_3$ | 0 | 0 | 0 | 0 | 73.24 | 26.76 |
| G | $K_3PO_4$ | 2.08 | 0 | 0 | 3.18 | 70.99 | 23.76 |

Reaction F showed the first observed complete conversion of the PEP025 intermediate to compound 4. This was accompanied by an estimated 26.76% of unidentified side-products (which were assigned an estimated response factor of 1 to facilitate calculations).

A number of different ways to prepare the ingenol-3,20-diangelate by organic synthesis can be contemplated. Starting from ingenol, different agents can be used to introduce the angelate. For example an activated angelic acid derivative such as angeloyl chloride. The esterification by reaction with angeloyl chloride can take place without an activator, or it can take place in the presence of a base such as pyridine or triethylamine, LiHMDS or DMAP, in a suitable solvent such as for example pyridine or THF. Another activated angelic acid derivative is angelic anhydride. The esterification by reaction with angelic anhydride can take place without a catalyst, or in the presence of an acidic catalyst using an acid such as perchlorid acid or a Lewis acid such as scandium(III) triflate or bismuth (III) triflate, or in the presence of a base such as sodium hdyrogencarbonate or triethyamine, LiHMDS, KHMDS, pyridine, cesium carbonate or DMAP, in a suitable solvent such as for example THF, MeCN, pyridine or MTBE. A mixed anhydride such as angeloyl trichlorobenzoyl anhydride, for example 2,4,6-trichlorobenzol anhydride can also be used. The esterification reaction can take place in the same conditions as mentioned above.

Also angelic acid in the presence of a coupling reagent can be useful. Coupling reagents in the form of carbodiimides, such as dicyclohexylcarbodiimide, EDCI (N-(3-dimethylaminopropyl)-N'-ethylcarbodiimide hydrochloride) with or without catalysts can be used. Suitable catalysts are for example 1-hydroxybenotriazole. Other coupling reagents for esterification can for example be 2-halo-1-alkylpyridinium salts such as 1-methyl-2-chloro-pyridinium iodide, or hydroxybenotrialzol derivatives such as HBTU (O-(benzotrialzol-1-yl)-N,N,N',N'-tetramethyluronium hexafluorophosphate, or HATU (N,N,N',N'-tetramethyl.O.(7-azabenzotriazol-1-yl)uranium hexafluorophosphate, or triazine derivatives such as DMTMM (4-(4,6-dimethoxy-1,3,5-triain-2-yl)-4-methylmorpholinium chloride. Suitable solvents can be methylene chloride, toluene, DMF or THF.

An illustrative example of the chemical synthesis of ingenol-3,20-diangelate from ingenol is:

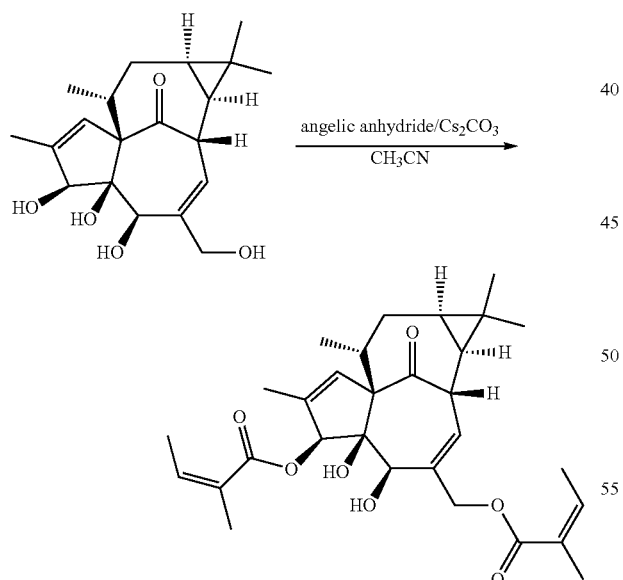

A mixture of ingenol (348 mg, 1 mmol), angelic anhydride (364 mg, 2 mmol) and cesium carbonate (1.0 g, 3.1 mmol) in acetonitrile (5 mL) was stirred at room temperature for 1 h. The mixture was diluted with Et$_2$O and the obtained mixture was washed with H$_2$O. The aqueous phase was extracted with Et$_2$O. The combined organic phases were dried over anhydrous sodium sulfate and concentrated in vacuo. The residue was purified by chromatography (petroleum ether/ethyl acetate 5:1), giving the title compound (245 mg, 48% yield) as a foam.

$^1$H NMR (300 MHz, CDCl$_3$) δ 6.30-5.93 (m, 4H), 5.57 (s, 1H), 4.86 (d, J=12.6 Hz, 1H), 4.57 (d, J=12.6 Hz, 1H), 4.13 (dd, J=11.7, 4.6 Hz, 1H), 3.90 (d, J=6.6 Hz, 1H), 3.72 (d, J=6.7 Hz, 1H), 3.49 (s, 1H), 2.60-2.45 (m, 1H), 2.27 (ddd, J=15.7, 9.1, 3.1 Hz, 1H), 2.01 (dd, J=7.3, 2.0 Hz, 3H), 1.98-1.90 (m, 6H), 1.90-1.85 (m, 3H), 1.79 (d, J=1.8 Hz, 3H), 1.77-1.70 (m, 1H), 1.08 (s, 3H), 1.06 (s, 3H), 0.98 (d, J=7.2 Hz, 3H), 0.94-0.83 (m, 1H), 0.70 (td, J=8.7, 6.2 Hz, 1H).

As an alternative embodiment, the following reaction pathway was investigated:

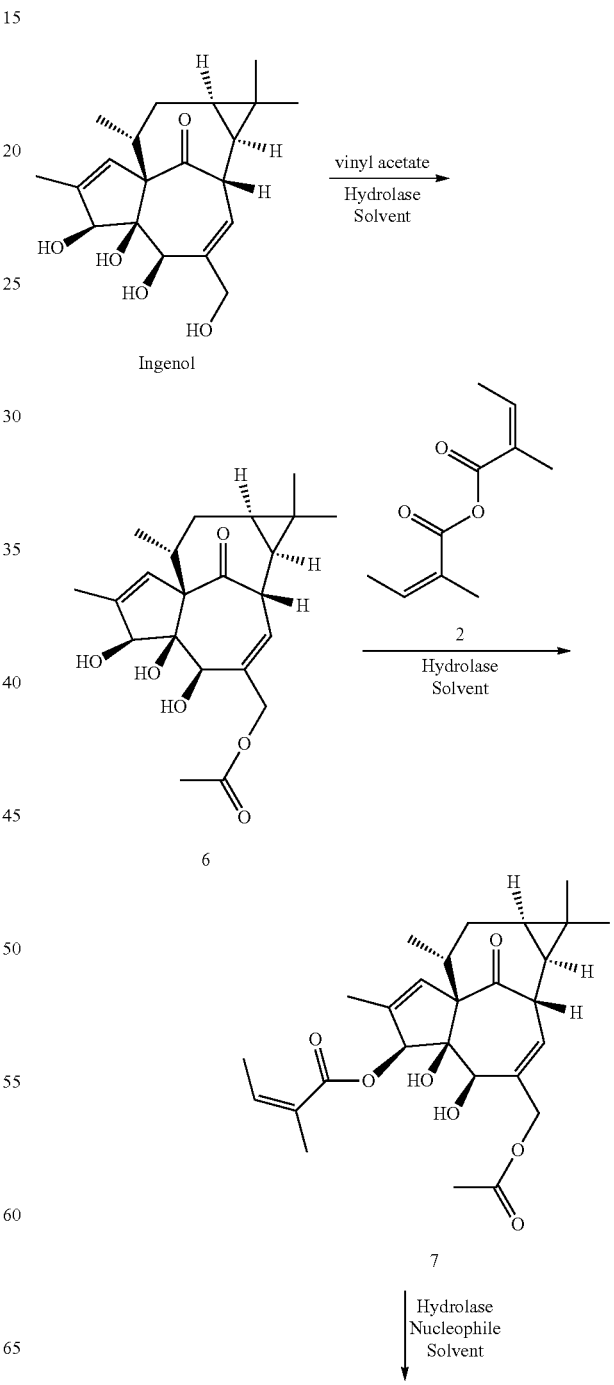

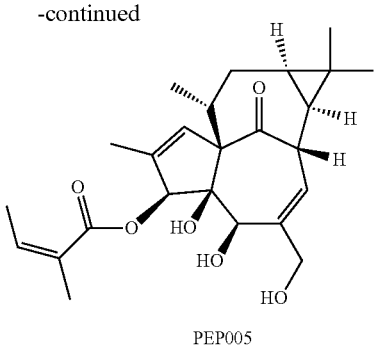

PEP005

In the following experiments starting by compound 6 the hydrolase reaction to compound 7 and deacetylation reaction to the final product is investigated.

Compound 6 was screened against 30 hydrolase enzymes in four different solvents (MTBE, heptane, toluene and acetonitrile) with angelic anhydride 2 as acyl donor. All screening reactions were carried out in HPLC vials. The general screening conditions are outlined below. Each screening reaction contained:

2 mg compound 6
1.5 eq. angelic anhydride 2 (1.4 mg)
1 small scoop of enzyme (if solid) or 2 drops (if liquid) (estimated ~10-20 mg)
2 or 3 pellets of 4 Å molecular sieves
0.5 mL solvent Enzyme and molecular sieves were added to the reaction vial first. For reactions in MTBE, toluene and acetonitrile (in which compound 6 was completely soluble), this was followed by 0.5 mL of a solution of compound 6 and angelic anhydride 2 in reaction solvent. For reactions in heptane (in which compound 6 was not completely soluble), compound 6 was measured into each individual vial, followed by 0.5 mL of a solution of angelic anhydride 2 in heptane.

Screening reactions were shaken at 30° C. for 66 hours and then analysed by TLC (eluent 1:1 EtOAc/heptane, visualised by phosphomolybdic acid stain and heating) followed by HPLC analysis (conditions given in Section 4).

For screening reactions in MTBE, heptane and toluene, HPLC samples were prepared by leaving reaction vials open in a well-ventilated fume hood to allow reaction solvent to evaporate, then adding 1.2 mL of a 1:1 mixture of 25 mM $KH_2PO_4$ buffer (pH 2.2)/acetonitrile. After thorough mixing, samples were centrifuged (5 minutes at 13,200 rpm) to remove any debris, then the supernatant taken and analysed by HPLC. This procedure ensured that the HPLC traces accurately showed the levels of different reaction components and avoided inaccuracies that could arise from reaction sampling, particularly in solvents where heterogeneity of some components would be an issue. For screening reactions in acetonitrile, it was not necessary to evaporate the solvent, and so 700 µL of a 1:1 mixture of 25 mM $KH_2PO_4$ buffer (pH 2.2)/acetonitrile was added to dilute the reaction mixture followed by centrifugation and submission of the supernatant for HPLC analysis.

Screening Results
Screening Reactions in MTBE

After TLC analysis it was immediately obvious that the desired transformation to compound 7 had not taken place to any significant degree. The reaction was sampled and analysed by LC-MS to reveal that the by-product had a mass of 430, which corresponded to the mass of PEP005, PEP015 or PEP025. After carrying out spiking studies, this product was confirmed to be PEP025.

The presence of this product demonstrated that the primary acetate on compound 6 was being enzymatically hydrolysed to form Ingenol, which was then undergoing acylation with angelic anhydride 2 to form PEP025. The spots of lowest $R_F$ visible on the TLC place were confirmed to be Ingenol by both TLC and HPLC analysis.

This indicates that the level of water in the solvent was high enough to allow enzymatic deacetylation to take place, even in the presence of 4 Å molecular sieves. It should be noted that an enzyme only needs the presence of one equivalent of water in order to do this. Traditionally, acetate is an easy protecting group to introduce enzymatically, but conversely it can also be easily removed. It was therefore considered that replacing this acetate with a larger acyl protecting group (such as butyrate) could prevent this undesired deacylation from occurring (see Sections 7, 8 & 9).

The HPLC results are summarized in Table 20. Reactions which gave no conversion were omitted.

For many of the reactions, a low level of an unidentified Ingenol-related product with a retention time of ~4.90 minutes was observed. This was assigned an estimated relative response factor of 1 to facilitate calculation of percentage conversions.

TABLE 20

Summary of screening reactions with compound 6 in MTBE with angelic anhydride 2 as acyl donor.

| | HPLC ANALYSIS (% conversion) | | | |
|---|---|---|---|---|
| EZYME | Ingenol | PEP025 | Cmpd 7 | Unknown (~4.90 min) |
| AH-01 | 6.97 | 88.14 | 0 | 0 |
| AH-02 | 12.23 | 0 | 1.16 | 0.85 |
| AH-03 | 43.71 | 41.35 | 0 | 0 |
| AH-04 | 4.57 | 93.31 | 0 | 2.13 |
| AH-05 | 1.19 | 0 | 0.70 | 0.57 |
| AH-06 | 0 | 0 | 0.30 | 2.00 |
| AH-07 | 16.16 | 0 | 0 | 0.55 |
| AH-08 | 23.85 | 31.69 | 0.15 | 1.14 |
| AH-09 | 1.45 | 0 | 0.09 | 0.69 |
| AH-10 | 0 | 100 | 0 | 0 |
| AH-11 | 0 | 0 | 0.29 | 0 |
| AH-17 | 0 | 0 | 0.39 | 0.19 |
| AH-24 | 1.07 | 10.02 | 0.04 | 2.15 |
| AH-32 | 0 | 0 | 0.29 | 0.11 |
| AH-33 | 0 | 0 | 0.54 | 0.67 |
| AH-35 | 11.82 | 0 | 0.62 | 0.62 |
| AH-36 | 0 | 0 | 0.63 | 0.41 |
| AH-37 | 0 | 0 | 0.23 | 0.16 |
| AH-39 | 49.64 | 41.43 | 0 | 1.22 |
| AH-40 | 58.40 | 20.36 | 0.07 | 1.17 |
| AH-44 | 9.53 | 0 | 0 | 0 |
| AH-48 | 0 | 0 | 0.33 | 0.15 |
| AH-49 | 33.85 | 52.31 | 0.10 | 0.91 |
| AH-50 | 87.20 | 3.19 | 0 | 0.07 |
| AH-51 | 71.87 | 0.28 | 0 | 0 |
| AH-54 | 2.20 | 0 | 0.47 | 0.41 |
| AH-55 | 65.76 | 11.62 | 0.07 | 0.26 |
| AH-57 | 14.13 | 0 | 0 | 0 |
| AH-58 | 41.53 | 0.49 | 0 | 0.46 |

Screening Reactions in Heptane

Due to heterogeneity in heptane, sampling of the screening reactions for TLC analysis could not be considered a reliable indication of the levels of various reaction components. Reactions were analysed by HPLC, the results of which are summarized in Table 21. Reactions which gave no conversion were omitted.

Many of the reactions exhibited the presence of low levels of two unidentified Ingenol-related products with retention times of ~4.45 and ~4.90 minutes, respectively. These were assigned estimated relative response factors of 1 to facilitate calculation of percentage conversions.

As with the screening reactions in MTBE, it was clear from these results that undesired enzymatic deacetylation of compound 6 took place for many of the reactions in heptane to form Ingenol. In most cases, subsequent acylation of Ingenol by angelic anhydride 2 then took place to varying degrees, forming a number of different products (mainly PEP025).

Reactions with AH-17, AH-32, AH-33 and AH-37 showed conversion of compound 6 to compound 7 without any apparent concurrent deacetylation to Ingenol. However, the levels of conversion were low (ranging from ~4-7%).

Once again it is clear that, for many of the reactions, undesired enzymatic deacetylation of compound 6 took place to form Ingenol, with varying degrees of subsequent acylation by angelic anhydride 2, mainly forming PEP025.

However, reactions with AH-17, AH-24, AH-32, AH-33 and AH-48 showed evidence of the selective acylation of compound 6 to compound 7 with conversions ranging from ~14-22%, without any evidence of concurrent deacetylation to Ingenol (although all five reactions also show the presence of the unknown side-product with a retention time of ~4.90

TABLE 21

Summary of screening reactions with compound 6 in heptane with angelic anhydride 2 as acyl donor.

| ENZYME | Ingenol | PEP005 | PEP015 | PEP025 | Cmpd 4 | Cmpd 7 | Unknown (~4.45 min) | Unknown (~4.90 min) |
|---|---|---|---|---|---|---|---|---|
| AH-01 | 33.08 | 1.21 | 0 | 11.41 | 0.98 | 2.23 | 0 | 0 |
| AH-02 | 54.26 | 1.71 | 0.47 | 7.91 | 0.42 | 2.10 | 0 | 0.25 |
| AH-03 | 68.06 | 0.32 | 0 | 17.75 | 0.39 | 0 | 0.28 | 0.35 |
| AH-04 | 3.96 | 0 | 0 | 92.36 | 0.49 | 0 | 0.61 | 2.58 |
| AH-05 | 3.87 | 0 | 0 | 4.20 | 0.58 | 6.59 | 0 | 0.85 |
| AH-06 | 8.62 | 0.02 | 0 | 10.01 | 0.03 | 0.42 | 0.36 | 1.79 |
| AH-07 | 61.87 | 0.60 | 0 | 10.11 | 0.40 | 1.35 | 0 | 0 |
| AH-08 | 20.64 | 0.29 | 0 | 71.12 | 1.56 | 0.25 | 0 | 1.13 |
| AH-09 | 4.26 | 0.05 | 0 | 1.52 | 0 | 1.53 | 0.30 | 1.28 |
| AH-10 | 38.78 | 0.39 | 0 | 55.46 | 0.57 | 0 | 0 | 0 |
| AH-11 | 17.70 | 0 | 0 | 0 | 0.22 | 2.32 | 0 | 0 |
| AH-17 | 0 | 0 | 0 | 0 | 0 | 4.45 | 0.19 | 1.12 |
| AH-24 | 1.06 | 0 | 0 | 1.34 | 0 | 0.83 | 0.20 | 1.01 |
| AH-32 | 0 | 0 | 0 | 0 | 0 | 4.28 | 0 | 1.13 |
| AH-33 | 0 | 0 | 0 | 0 | 0 | 6.89 | 0 | 1.14 |
| AH-35 | 37.15 | 0.26 | 0 | 9.19 | 0.24 | 1.65 | 0 | 0.47 |
| AH-36 | 1.05 | 0 | 0 | 0 | 0 | 1.30 | 0 | 0.39 |
| AH-37 | 0 | 0 | 0 | 0 | 0 | 7.05 | 0 | 1.22 |
| AH-39 | 70.47 | 0 | 0 | 6.78 | 0 | 0 | 0 | 0 |
| AH-40 | 74.47 | 0 | 0 | 8.94 | 0 | 0 | 0 | 0.49 |
| AH-44 | 63.95 | 0 | 0 | 0 | 0 | 0 | 0 | 0 |
| AH-49 | 43.83 | 0 | 0 | 22.68 | 0 | 0 | 0 | 0.27 |
| AH-50 | 79.32 | 0 | 0 | 0.19 | 0 | 0 | 0 | 0 |
| AH-51 | 78.03 | 0 | 0 | 0 | 0 | 0 | 0 | 0 |
| AH-54 | 2.29 | 0 | 0 | 0 | 0 | 2.89 | 0.09 | 0.79 |
| AH-55 | 62.42 | 0 | 0 | 0.78 | 0 | 0 | 0 | 0 |
| AH-57 | 16.61 | 0 | 0 | 1.69 | 0 | 0 | 0 | 0 |
| AH-58 | 65.16 | 0 | 0 | 1.42 | 0 | 0 | 0 | 0.17 |

Screening Reactions in Toluene

The HPLC results are summarized in Table 22. Reactions which gave no conversion were omitted.

mins). These are the most encouraging results for this route to date. Interestingly, each of these enzymes had previously shown ability to selectively acylate Ingenol to PEP005 in acetonitrile, albeit in very low levels (<5% conversion).

TABLE 22

Summary of screening reactions with compound 6 in toluene with angelic anhydride 2 as acyl donor (most promising results highlighted).

| ENZYME | Ingenol | PEP005 | PEP015 | PEP025 | Cmpd 4 | Cmpd 7 | Unknown (~4.45 min) | Unknown (~4.90 min) |
|---|---|---|---|---|---|---|---|---|
| AH-01 | 64.70 | 1.47 | 0 | 23.39 | 0.70 | 0 | 0 | 0.49 |
| AH-02 | 60.86 | 3.90 | 0.49 | 18.55 | 1.96 | 1.29 | 0 | 0.96 |
| AH-03 | 68.92 | 0.71 | 0 | 27.62 | 0.30 | 0 | 0 | 0.51 |
| AH-04 | 11.22 | 0 | 0 | 85.75 | 0 | 0 | 0 | 0.83 |
| AH-05 | 0 | 0 | 0 | 4.57 | 0.84 | 10.59 | 0 | 0.37 |
| AH-06 | 16.21 | 0 | 0 | 8.17 | 0 | 0 | 0.23 | 2.04 |
| AH-07 | 63.37 | 2.52 | 0.56 | 10.35 | 1.68 | 1.11 | 0 | 0.39 |
| AH-08 | 38.24 | 0.66 | 0 | 49.19 | 1.74 | 0.47 | 0 | 0.67 |
| AH-09 | 26.43 | 0 | 0 | 9.21 | 0 | 0 | 0.39 | 1.81 |
| AH-10 | 31.63 | 0 | 0 | 66.71 | 0.28 | 0 | 0 | 0 |

TABLE 22-continued

Summary of screening reactions with compound 6 in toluene with angelic anhydride 2 as acyl donor (most promising results highlighted).

| ENZYME | Ingenol | PEP005 | PEP015 | PEP025 | Cmpd 4 | Cmpd 7 | Unknown (~4.45 min) | Unknown (~4.90 min) |
|---|---|---|---|---|---|---|---|---|
| AH-11 | 6.09 | 0 | 0 | 0.58 | 0 | 4.56 | 0 | 2.09 |
| AH-17 | 0 | 0 | 0 | 0 | 0 | 22.25 | 0 | 1.51 |
| AH-24 | 0 | 0 | 0 | 0 | 0 | 18.44 | 0 | 2.09 |
| AH-32 | 0 | 0 | 0 | 0 | 0 | 21.21 | 0 | 1.88 |
| AH-33 | 0 | 0 | 0 | 0 | 0 | 14.64 | 0 | 1.50 |
| AH-35 | 74.05 | 0.93 | 0 | 7.57 | 0.31 | 0.63 | 0 | 0.43 |
| AH-36 | 3.82 | 0 | 0 | 4.49 | 1.63 | 10.35 | 0 | 1.53 |
| AH-37 | 0 | 0 | 0 | 2.41 | 0.45 | 12.07 | 0 | 1.92 |
| AH-39 | 36.84 | 0 | 0 | 60.90 | 0 | 0 | 0 | 0 |
| AH-40 | 55.02 | 0 | 0 | 38.45 | 0 | 0 | 0 | 1.27 |
| AH-44 | 74.94 | 0 | 0 | 0 | 0 | 0 | 0 | 0 |
| AH-48 | 0 | 0 | 0 | 0 | 0.15 | 20.87 | 0 | 1.57 |
| AH-49 | 48.75 | 0 | 0 | 39.67 | 0 | 0 | 0 | 0 |
| AH-50 | 85.13 | 0 | 0 | 2.21 | 0 | 0 | 0 | 0 |
| AH-51 | 73.45 | 0 | 0 | 0 | 0 | 0 | 0 | 0 |
| AH-54 | 19.27 | 0 | 0 | 7.00 | 0.12 | 1.36 | 0 | 0.32 |
| AH-55 | 68.62 | 0 | 0 | 28.28 | 0 | 0 | 0 | 0.26 |
| AH-57 | 52.19 | 0 | 0 | 5.44 | 0 | 0 | 0 | 0 |
| AH-58 | 60.07 | 0 | 0 | 1.05 | 0 | 0.24 | 0 | 0.14 |

1.2.1. Screening Reactions in Acetonitrile

The HPLC results are summarized in Table 23. Reactions which gave no conversion were omitted. There were no reactions that showed a significant degree of compound 7 formation

TABLE 23

Summary of screening reactions with compound 6 in acetonitrile with angelic anhydride 2 as acyl donor.

| ENZYME | Ingenol | PEP005 | PEP025 | Cmpd 4 | Cmpd 7 | Unknown (~4.90 min) |
|---|---|---|---|---|---|---|
| AH-01 | 7.37 | 0 | 0 | 0 | 1.57 | 0 |
| AH-02 | 3.39 | 0 | 0 | 0 | 2.41 | 0 |
| AH-03 | 50.60 | 0.69 | 15.94 | 0.13 | 0.47 | 0 |
| AH-04 | 4.68 | 0 | 93.64 | 0 | 0 | 0 |
| AH-05 | 0 | 0 | 0 | 0 | 0.93 | 0 |
| AH-08 | 5.61 | 0 | 0 | 0 | 0.90 | 0.33 |
| AH-09 | 1.03 | 0 | 0 | 0 | 0 | 0 |
| AH-10 | 10.74 | 0 | 19.93 | 0 | 1.14 | 0 |
| AH-11 | 0 | 0 | 0 | 0 | 2.58 | 0 |
| AH-17 | 0 | 0 | 0 | 0 | 0.88 | 0 |
| AH-24 | 0 | 0 | 0 | 0 | 0.47 | 0 |
| AH-32 | 0 | 0 | 0 | 0 | 0.93 | 0 |
| AH-35 | 0 | 0 | 0 | 0 | 0.36 | 0 |
| AH-37 | 0 | 0 | 0 | 0 | 1.68 | 0 |
| AH-39 | 0 | 0 | 84.05 | 0 | 0 | 0 |
| AH-40 | 8.99 | 0 | 0 | 0 | 0 | 0 |
| AH-48 | 0 | 0 | 0 | 0 | 1.09 | 0 |
| AH-49 | 28.90 | 0 | 45.49 | 0.11 | 0 | 0 |
| AH-50 | 24.87 | 0 | 45.21 | 0 | 0 | 0 |
| AH-51 | 56.00 | 0 | 11.82 | 0 | 0 | 0 |
| AH-54 | 0 | 0 | 0 | 0 | 2.32 | 0 |
| AH-55 | 31.33 | 0 | 50.30 | 0 | 0 | 0 |
| AH-57 | 5.73 | 0 | 5.39 | 0 | 0 | 1.82 |
| AH-58 | 2.03 | 0 | 1.24 | 0 | 0 | 0 |

1.3. Further Investigation of Screening Reactions in Toluene

The most promising screening reactions on compound 6 were with hydrolases AH-17, AH-24, AH-32, AH-33 and AH-48 in toluene. These reactions showed evidence of the selective acylation of compound 6 to compound 7 with conversions ranging from ~14-22%, without any evidence of concurrent deacetylation to Ingenol (although all five reactions also showed the presence of the unknown side-product with a retention time of ~4.90 mins). Therefore some further investigation was carried out.

1.3.1. Temperature Experiments

It was decided to carry out reactions with hydrolases AH-17, AH-24, AH-32, AH-33 and AH-48 in toluene at 30° C., 40° C. and 50° C. in order to see if the level of conversion to compound 7 could be pushed further.

Reaction conditions were the same as those described in Section 6.1 (except for the differing reaction temperatures). Reactions were shaken for 90 hours and then analysed by TLC (eluent 1:1 EtOAc/heptane, visualised by phosphomolybdic acid stain and heating). Only faint spots of compound 7 were visible. Reactions were prepared for HPLC analysis by rapidly evaporating the toluene with a directed stream of nitrogen, then dissolving the residue in a 1:1 mixture of 25 mM $KH_2PO_4$ buffer (pH 2.2)/acetonitrile. This solution was centrifuged (5 minutes at 13,200 rpm) to remove any debris, then the supernatant was analysed.

The results are summarized in Table 24.

Surprisingly, conversion to compound 7 was found to be <1% for all reactions. This is a big difference from the conversions previously observed in the original screening reactions (14-20%). The only difference between the two sets of experiments (aside from changes in temperature) is that the original screens were allowed to evaporate slowly at room temperature in a well-ventilated fume hood over 2 days before preparation of HPLC samples, whereas the temperature experiments were evaporated rapidly with a directed stream of nitrogen. It is believed that as the level of toluene in the original screens slowly decreased, the concentration increased to a point where the reaction occurred more rapidly, even without agitation or elevated temperature. This hypothesis is supported by looking at the original TLC analysis of the screening reactions, where the spots of compound 7 are fainter than would be expected for conversions of up to 20%.

This suggests that conversions were much lower when the initial TLC analysis was carried out.

Therefore it was decided to carry out some experiments at higher concentration to investigate this (see Sections 6.3.2 and 6.3.3).

TABLE 24

Summary of temperature experiments with compound 6 in toluene with hydrolases AH-17, AH-24, AH-32, AH-33 and AH-48.

| TEMP | | HPLC ANALYSIS (% conversion) | |
|---|---|---|---|
| (° C.) | ENZYME | Cmpd 7 | (~4.90 min) |
| 30 | AH-17 | 0.61 | 1.65 |
|  | AH-24 | 0.59 | 2.20 |
|  | AH-32 | 0.54 | 2.21 |
|  | AH-33 | 0.35 | 1.82 |
|  | AH-48 | 0.27 | 1.46 |
| 40 | AH-17 | 0.26 | 1.17 |
|  | AH-24 | 0.40 | 2.29 |
|  | AH-32 | 0.41 | 2.37 |
|  | AH-33 | 0.51 | 1.62 |
|  | AH-48 | 0.38 | 1.30 |
| 50 | AH-17 | 0.17 | 0.14 |
|  | AH-24 | 0.68 | 2.64 |
|  | AH-32 | 0.72 | 2.90 |
|  | AH-33 | 0.96 | 2.75 |
|  | AH-48 | 0.42 | 1.77 |

1.3.2. High Concentration Experiments

Set 1

Following on from the temperature experiments, it was decided to carry out reactions with these five enzymes at much higher concentration of compound 6 (ten times the concentration of the original screening reactions, i.e. 20 mg/reaction). The loading of enzyme (50% w/w with respect to compound 6) was also proportionally much less than in the original screening reactions as very high enzyme loadings would not be preferable for larger scale synthesis.

All reactions were carried out in HPLC vials. The conditions are outlined below. Each screening reaction contained:
20 mg compound 6
1.2 eq. angelic anhydride 2 (11.2 mg)
10 mg enzyme (weighed exactly) (50% w/w)
2 or 3 pellets of 4 Å molecular sieves
0.5 mL toluene Enzyme, compound 6 and molecular sieves were added to the reaction vial first, followed by 0.5 mL of a solution of angelic anhydride 2 in toluene. Reactions were shaken overnight (18 hours) at 30° C., then a 30 µL sample was taken. This sample was evaporated by a directed stream of nitrogen, then redissolved in a 1:1 mixture of 25 mM $KH_2PO_4$ (pH 2.2)/acetonitrile, centrifuged (5 minutes at 13,200 rpm) to remove debris, and submitted for HPLC analysis. Disappointingly, conversions for all reactions were <1%. Therefore it was decided to increase the temperature to 50° C. and allow the reactions to continue, with 30 µL samples taken periodically for HPLC analysis. The results are summarized in Table 25.

It can be seen that the level of compound 7 steadily increased over time after the temperature was increased to 50° C., although reaction rates were slow (the fastest reaction with AH-33 only reaching ~42% conversion after 19 days) Additionally, the level of the unidentified Ingenol-related side-product at ~4.90 minutes was observed to increase significantly over time, reaching as high as ~20-31% after 19 days.

TABLE 25

Summary of high concentration experiments with compound 6 in toluene with hydrolases AH-17, AH-24, AH-32, AH-33 and AH-48 (50% w/w).

| | | HPLC ANALYSIS (% conversion) | |
|---|---|---|---|
| ENZYME | TIME (DAYS) | Cmpd 7 | Unknown (~4.90 min) |
| AH-17 | 1 | 0.32 | 0.35 |
|  | 2 | 3.56 | 1.67 |
|  | 5 | 13.13 | 5.70 |
|  | 8 | 20.55 | 9.30 |
|  | 13 | 29.28 | 16.09 |
|  | 19 | 35.90 | 22.83 |
| AH-24 | 1 | 0.29 | 0.27 |
|  | 2 | 2.33 | 1.62 |
|  | 5 | 9.61 | 4.83 |
|  | 8 | 15.62 | 8.19 |
|  | 13 | 22.96 | 14.09 |
|  | 19 | 29.44 | 20.88 |
| AH-32 | 1 | 0.40 | 0.37 |
|  | 2 | 3.31 | 1.91 |
|  | 5 | 14.49 | 7.15 |
|  | 8 | 24.09 | 13.52 |
|  | 13 | 33.77 | 22.16 |
|  | 19 | 41.38 | 31.58 |
| AH-33 | 1 | 0.30 | 0.27 |
|  | 2 | 3.21 | 1.75 |
|  | 5 | 15.04 | 6.59 |
|  | 8 | 24.77 | 11.51 |
|  | 13 | 34.05 | 18.46 |
|  | 19 | 42.12 | 26.09 |
| AH-48 | 1 | 0.39 | 0.33 |
|  | 2 | 4.02 | 1.85 |
|  | 5 | 14.32 | 6.50 |
|  | 8 | 21.95 | 11.37 |
|  | 13 | 29.88 | 18.37 |
|  | 19 | 36.92 | 25.16 |

1.3.3. High Concentration Experiments

Set 2

Following on from the results of Set 1, further experiments were carried out at the same high concentration of compound 6 (20 mg/reaction), but with a larger loading of enzyme (40 mg/reaction, i.e. 200% w/w with respect to compound 6). It is not uncommon for hydrolase-mediated reactions to be carried out at such high loadings of enzyme, and the cost contribution of the enzyme can be relatively low.

Reactions were shaken at 50° C. with 30 µL samples taken periodically for HPLC analysis. The results are summarized in Table 26.

TABLE 26

Summary of high concentration experiments with compound 6 in toluene with hydrolases AH-17, AH-24, AH-32, AH-33 and AH-48 (200% w/w).

| | | HPLC ANALYSIS (% conversion) | |
|---|---|---|---|
| ENZYME | TIME (DAYS) | Cmpd 7 | Unknown (~4.90 min) |
| AH-17 | 5 | 16.33 | 6.02 |
|  | 11 | 28.79 | 12.53 |
| AH-24 | 5 | 8.26 | 3.65 |
|  | 11 | 13.85 | 5.56 |
| AH-32 | 5 | 19.16 | 9.00 |
|  | 11 | 35.25 | 19.94 |
| AH-33 | 5 | 19.41 | 8.15 |
|  | 11 | 36.00 | 18.63 |
| AH-48 | 5 | 23.86 | 11.84 |
|  | 11 | 40.28 | 25.86 |

Once again, a steady increase in the level of compound 7 formation was observed over time. Although the reaction rates were notably faster than the corresponding reactions with 50% (w/w) loading of enzyme, the conversions after 11 days were still unsatisfactory. Once again, the level of the unidentified Ingenol-related side-product at ~4.90 minutes was observed to increase significantly over time, reaching as high as ~25% with AH-48 after 11 days.

Screening reactions on compound 6 revealed that, in many cases, the primary acetate was being enzymatically hydrolysed to form Ingenol, which was then undergoing acylation with angelic anhydride 2 to form mainly PEP025. This reaction sequence rendered the primary acetate ineffective as a protecting group.

Traditionally, acetate is an easy protecting group to introduce enzymatically, but conversely it can also be easily removed. It was considered a distinct possibility that replacing this acetate with a larger acyl protecting group would prevent this undesired deacylation from occurring. Therefore it was decided to carry out screening reactions on compound 8 and 10 and 12, on which the primary hydroxyl in position 20 was protected with a butyrate ester, a pivalate ester or a benzoate ester respectively.

Synthesis of Compound 8

Ingenol (300 mg, 0.861 mmol) was added to a 50 mL falcon tube along with a large spatula of 4 Å molecular sieves, followed by hydrolase AH-04 (1 g) and a solution of vinyl butyrate (1.97 g, 17.22 mmol, 20 equivalents) in MTBE (25 mL). The tube was sealed tight and shaken for 66 hours at 30° C., after which TLC analysis was carried out (eluent 1:1 EtOAc/heptane, visualized by phosphomolybdic acid stain and heating.

This revealed that the reaction had essentially proceeded to completion (with just a very faint spot for remaining starting material). The reaction mixture was then filtered to remove enzyme and adsorbed onto silica (~1 g), then purified by silica chromatography (eluent gradient from 100% hexane to 7:3 hexane/EtOAc) to afford compound 8 (329 mg, 0.786 mmol, 91% yield) as a pale yellow gum.

Synthesis of Compound 10

Ingenol (300 mg, 0.861 mmol) was added to a 50 mL falcon tube along with a large spatula of 4 Å molecular sieves, followed by hydrolase AH-04 (1 g) and a solution of vinyl pivalate (2.21 g, 17.22 mmol, 20 equivalents) in MTBE (25 mL). The tube was sealed tight and shaken for 17 hours at 37° C., after which TLC analysis was carried out (eluent 1:1 EtOAc/heptane, visualized by phosphomolybdic acid stain and heating)

This revealed that the reaction had essentially proceeded to completion (with just a faint spot for remaining starting material). The reaction mixture was then filtered to remove enzyme and adsorbed onto silica (~1.5 g), then purified by silica chromatography (eluent gradient from 100% hexane to 7:3 hexane/EtOAc) to afford compound 10 (271 mg, 0.627 mmol, 73% yield) as a pale yellow gum.

Compound 12 was prepared by the following procedure.

Ingenol (260 mg, 0.746 mmol) was added to a 50 mL glass bottle along with a large spatula of 4 Å molecular sieves, followed by hydrolase AH-04 (1 g) and a solution of vinyl benzoate (2.21 g, 14.92 mmol, 20 equivalents) in MTBE (25 mL). The bottle was sealed tight and shaken for 16 hours at 37° C., after which TLC analysis was carried out (eluent 1:1 EtOAc/heptane, visualized by phosphomolybdic acid stain and heating). This revealed that the reaction had essentially proceeded to completion (with just a faint spot for remaining starting material). The reaction mixture was then filtered to remove enzyme and adsorbed onto silica (~1.5 g), then purified by silica chromatography (eluent gradient from 100% hexane to 1:1 hexane/EtOAc) to afford compound 12 (301 mg, 0.665 mmol, 89% yield) as a pale yellow gum.

Screening Conditions

Compound 8, 10 and 12 were screened against 30 hydrolase enzymes in two different solvents (MTBE and toluene) with angelic anhydride 2 as acyl donor. All screening reactions were carried out in HPLC vials. The general screening conditions are outlined below. Each screening reaction contained:

2 mg compound 8
1.5 eq. angelic anhydride 2 (1.31 mg)
1 small scoop of enzyme (if solid) or 2 drops (if liquid) (estimated ~10-20 mg)
2 or 3 pellets of 4 Å molecular sieves
0.5 mL solvent Enzyme and molecular sieves were added to the reaction vial first, followed by 0.5 mL of a solution of compound 8 and angelic anhydride 2 in reaction solvent.

Screening reactions were shaken at around 30-40° C. for 64-138 hours depending on the starting material and then analysed by TLC (eluent 1:1 EtOAc/heptane, visualised by phosphomolybdic acid stain and heating).

Screening Results

Screening Reactions in MTBE

It was immediately obvious that the desired transformation to the desired compounds had not taken place to any discernable level. It was clear that many of the enzymes had enzymatically hydrolysed the primary protecting group (in this case butyrate) to form Ingenol, which then underwent acylation with angelic anhydride 2 to form PEP025.

Spots for both Ingenol and PEP025 were clearly visible in TLC. This demonstrated that replacing the primary acetate with a butyrate conferred no discernable advantage with regard to hydrolytic stability.

Screening Reactions in Toluene

As seen for the screening reactions in MTBE, it was clear that many of the enzymes had enzymatically hydrolysed the 20-acyl protecting group to form Ingenol, which then underwent acylation with angelic anhydride 2 to form PEP025. Some very faint spots of high enough $R_F$ to likely correspond to desired product were discernable, although at a level considered to be insignificant.

Deacylation from ingenol-3,20-diangelate:

Deacylation Screening in Organic Solvent with 20% $H_2O$

A number of initial deacylation screening reactions were carried out in organic solvent (acetonitrile or MTBE) containing 20% $H_2O$ (as 25 mM $KH_2PO_4$ buffer at pH 5) with 30 different hydrolase enzymes. Each screening reaction containing the following:

2 mg ingenol-3,20-diangelate
1 small scoop of enzyme (if solid) or 2 drops (if liquid)
0.4 mL organic solvent
0.1 mL $KH_2PO_4$ buffer (25 mM, pH 5)

Enzyme was added to the reaction vial first, followed by 0.4 mL of a stock solution of ingenol-3,20-diangelate in organic solvent then 0.1 mL of 25 mM $KH_2PO_4$ buffer (pH 5).

Screening reactions were shaken at 28-30° C. for 3-4 days, then analysed by TLC (eluent 1:1 EtOAc/heptane, visualized by phosphomolybdic acid stain and heating).

Deacylation Screening Reactions in Acetonitrile with 20% $H_2O$

Reactions were shaken at 28° C. for 17 hours then analysed by TLC. No spots of deacylation products were observed, so shaking was continued for a further 77 hours and the reactions re-analysed by TLC A total of three reactions (06, 09 & 24) appeared to show the appearance of a faint spot corresponding to the $R_F$ of ingenol-3-angelate. HPLC analysis revealed this to be the case, although the level of conversion was very low. Another Ingenol-related side product (showing the characteristic UV absorbance at ~291 nm) was observed in all three reactions. It is believed that this corresponded to the TLC spot beneath that of ingenol-3,20-diangelate (especially visible for the reactions with 03 and 04). HPLC analysis of the reaction with 04 confirmed this to be the case This compound was previously observed in acylation reactions of Ingenol with angelic anhydride and hydrolase 54 in the presence of the cationic surfactant CTAB, and was tentatively identified as diacylated compound 5. This was assigned an estimated relative response factor of 1 to facilitate calculation of percentage conversions.

The presence of compound 5 would imply that acyl migration was taking place under these conditions

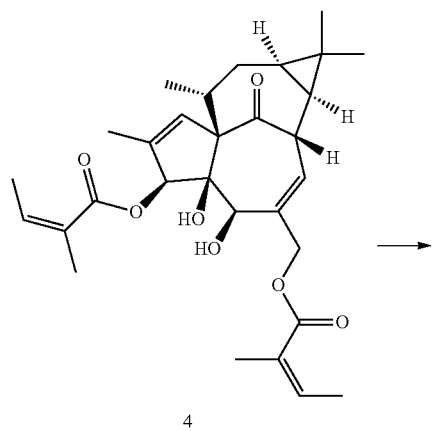

4

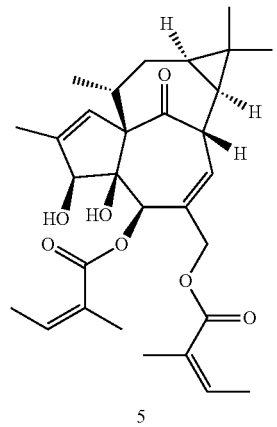

5

A summary of the HPLC using Method B results for the screening reactions is shown in Table 27.

TABLE 27

Summary of results for deacylation screening reactions of ingenol-3,20-diangelate in acetonitrile containing 20% $H_2O$.

| ENZYME | HPLC ANALYSIS (% conversion) | | | | |
|---|---|---|---|---|---|
| | Ingenol | ingenol-3-angelate | PEP015 | PEP025 | Cmpd 5 |
| 06 | 0 | 1.56 | 0 | 0 | 0.36 |
| 09 | 0 | 0.64 | 0 | 0 | 1.48 |

TABLE 27-continued

Summary of results for deacylation screening reactions of ingenol-3,20-diangelate in acetonitrile containing 20% $H_2O$.

| ENZYME | HPLC ANALYSIS (% conversion) | | | | |
|---|---|---|---|---|---|
| | Ingenol | ingenol-3-angelate | PEP015 | PEP025 | Cmpd 5 |
| 24 | 0 | 1.18 | 0 | 0 | 0.31 |
| BLANK | 0 | 0 | 0 | 0 | 1.35 |

Deacylation Screening Reactions in MTBE with 20% $H_2O$

Reactions were shaken at 30° C. for 94 hours then analysed by TLC.

TABLE 28

Summary of results for deacylation screening reactions of ingenol-3,20-diangelate in MTBE containing 20% $H_2O$.

| ENZYME | Ingenol | ingenol-3-angelate | PEP015 | PEP025 | Cmpd 5 |
|---|---|---|---|---|---|
| 06 | 0 | 3.28 | 0 | 0 | 0 |
| 09 | 0 | 5.78 | 0 | 0 | 0 |
| 24 | 0 | 2.49 | 0 | 0 | 0 |

Deacylation Screening in MTBE with 5% Nucleophile

A series of further screening reactions were carried out with these three enzymes in MTBE containing 5% (v/v) nucleophile for deacylation. The three nucleophiles investigated were water (for deacylation by hydrolysis), ethanol and butanol (for deacylation by transesterification). A larger loading of enzyme was used (3 times the previous amount).

Each screening reaction containing the following:

2 mg ingenol-3,20-diangelate 3 small scoops of enzyme

475 µL MTBE

25 µL $KH_2PO_4$ buffer (25 mM, pH 5), EtOH or BuOH

Enzyme was added to the reaction vial first, followed by 475 µL of a stock solution of ingenol-3,20-diangelate in MTBE, then 25 µL of nucleophile. Reactions were shaken at 30° C. for 40 hours, then 100 µL of reaction mixture was taken for HPLC analysis. Reactions were continued for a further 77 hours, then analysed again by HPLC.

HPLC samples were prepared by allowing the solvent to evaporate in a well-ventilated fume hood, or by blowing with a stream of nitrogen, then dissolving the residue in 100 µL DMSO and diluting with ~1 mL 25 mM $KH_2PO_4$ buffer (pH 2.2)/acetonitrile (1:1). This was mixed thoroughly then filtered through a glass pipette containing a cotton wool plug into an HPLC vial.

A summary of results is shown in Table 29.

TABLE 29

Summary of results for deacylation screening reactions of ingenol-3,20-diangelate with 06, AH09 & 24 in MTBE containing 5% H$_2$O, EtOH or BuOH as nucleophile.

| ENZYME | NUCLEOPHILE | REACTION TIME (HOURS) | HPLC ANALYSIS (% conversion) | | | |
|---|---|---|---|---|---|---|
| | | | Ingenol | ingenol-3-angelate | PEP015 | PEP025 |
| 06 | H$_2$O | 40 | 0 | 3.11 | 0 | 0 |
| | | 117 | 0 | 7.43 | 0 | 0 |
| | EtOH | 40 | 0 | 0.81 | 0 | 0 |
| | | 117 | 0 | 2.59 | 0 | 0 |
| | BuOH | 40 | 0 | 8.80 | 0 | 0 |
| | | 117 | 0 | 23.99 | 0 | 0 |
| 09 | H$_2$O | 40 | 0 | 2.98 | 0 | 0 |
| | | 117 | 0 | 8.54 | 0 | 0 |
| | EtOH | 40 | 0 | 0.25 | 0 | 0 |
| | | 117 | 0 | 0.53 | 0 | 0 |
| | BuOH | 40 | 0 | 2.68 | 0 | 0 |
| | | 117 | 0 | 7.79 | 0 | 0 |
| 24 | H$_2$O | 40 | 0 | 3.03 | 0 | 0 |
| | | 117 | 0 | 7.46 | 0 | 0 |
| | EtOH | 40 | 0 | 0.23 | 0 | 0 |
| | | 117 | 0 | 0.55 | 0 | 0 |
| | BuOH | 40 | 0 | 1.36 | 0 | 0 |
| | | 117 | 0 | 17.97 | 0 | 0 |

Deacylation Screening in Various Solvents with Butanol as Nucleophile

Each reaction contained:
1 mg ingenol-3,20-diangelate
1 small scoop of 06
487.5 µL solvent+12.5 µL butanol (2.5% v/v)
OR 475 µL solvent+25 µL butanol (5% v/v)
OR 450 µL solvent+50 µL butanol (10% v/v)
Six solvents were investigated:
MTBE
Methyl-THF
Ethyl acetate
Acetonitrile
Heptane
Toluene
(Ingenol-3,20-diangelate was soluble in all six solvents).
Enzyme was added to the reaction vial first, followed by 450 µL of a stock solution of ingenol-3,20-diangelate in solvent and then butanol (either 12.5 µL, 25 µL or 50 µL). Reactions were topped up with solvent to a total volume of 500 µL as needed. Reactions were shaken at 30° C. for a total of 160 hours (7 days), with 100 µL samples being taken for HPLC analysis after 40 hours and 112 hours, followed by a final analysis.
A summary of results is shown in Table 30.
These reactions were carried out in parallel with those described above.

TABLE 30

Summary of results for deacylation screening reactions of ingenol-3,20-diangelate with 06 in various solvents containing butanol as nucleophile.

| SOLVENT | % (v/v) BUTANOL | REACTION TIME (HOURS) | HPLC ANALYSIS (% conversion) | | | |
|---|---|---|---|---|---|---|
| | | | Ingenol | ingenol-3-angelate | PEP015 | PEP025 |
| MTBE | 2.5 | 40 | 0 | 6.95 | 0 | 0 |
| | | 112 | 0 | 22.78 | 0 | 0 |
| | | 160 | 0 | 36.67 | 0 | 0 |
| | 5 | 40 | 0 | 1.90 | 0 | 0 |
| | | 112 | 0 | 5.45 | 0 | 0 |
| | | 160 | 0 | 8.90 | 0 | 0 |
| | 10 | 40 | 0 | 1.29 | 0 | 0 |
| | | 112 | 0 | 3.35 | 0 | 0 |
| | | 160 | 0 | 5.77 | 0 | 0 |
| Me-THF | 2.5 | 40 | 0 | 0 | 0 | 0 |
| | | 112 | 0 | 0.27 | 0 | 0 |
| | | 160 | 0 | 0.86 | 0 | 0 |
| | 5 | 40 | 0 | 0 | 0 | 0 |
| | | 112 | 0 | 0.36 | 0 | 0 |
| | | 160 | 0 | 1.05 | 0 | 0 |
| | 10 | 40 | 0 | 0 | 0 | 0 |
| | | 112 | 0 | 0.28 | 0 | 0 |
| | | 160 | 0 | 0.80 | 0 | 0 |
| Heptane | 2.5 | 40 | 0 | 20.54 | 0 | 0 |
| | | 112 | 0 | 54.67 | 0 | 0 |
| | | 160 | 0 | 79.35 | 0 | 0 |
| | 5 | 40 | 0 | 8.28 | 0 | 0 |
| | | 112 | 0 | 30.33 | 0 | 0 |
| | | 160 | 0 | 58.94 | 0 | 0 |
| | 10 | 40 | 0 | 2.43 | 0 | 0 |
| | | 112 | 0 | 8.04 | 0 | 0 |
| | | 160 | 0 | 18.65 | 0 | 0 |
| Toluene | 2.5 | 40 | 0 | 0.90 | 0 | 0 |
| | | 112 | 0 | 2.84 | 0 | 0 |
| | | 160 | 0 | 5.52 | 0 | 0 |
| | 5 | 40 | 0 | 0.53 | 0 | 0 |
| | | 112 | 0 | 1.36 | 0 | 0 |
| | | 160 | 0 | 3.19 | 0 | 0 |
| | 10 | 40 | 0 | 0.19 | 0 | 0 |
| | | 112 | 0 | 0.48 | 0 | 0 |
| | | 160 | 0 | 0.98 | 0 | 0 |

Deacylation Screening in MTBE with Various Alcohols as Nucleophile

The following experiments were performed with 06 in MTBE utilizing longer chain alcohols as nucleophile for the deacylation. The amounts of alcohol were also varied.

Each reaction contained:
1 mg ingenol-3,20-diangelate
1 small scoop of O6
487.5 μL MTBE+12.5 μL alcohol (2.5% v/v)
OR 475 μL MTBE+25 μL alcohol (5% v/v)
OR 450 μL MTBE+50 μL alcohol (10% v/v)

Three alcohols were investigated as nucleophile for the deacylation:
1-Pentanol
1-Hexanol
1-Octanol Enzyme was added to the reaction vial first, followed by 450 μL of a stock solution of ingenol-3,20-diangelate in MTBE and then the appropriate alcohol (either 12.5 μL, 25 μL or 50 μL). Reactions were topped up with MTBE to a total volume of 500 μL as needed. Reactions were shaken at 30° C. for a total of 160 hours (7 days), with 100 μL samples being taken for HPLC analysis after 40 hours and 112 hours, followed by a final analysis.

A summary of results is shown in Table 31. Results of reactions in the presence of butanol (from Section 11.3) are also added for direct comparison These reactions were carried out in parallel with those described in Section 11.3.

Deacylation Screening in Heptane with Various Alcohols as Nucleophile

The following reactions were carried out with 1% and 2.5% (v/v) alcohol.

Each reaction contained:
1 mg ingenol-3,20-diangelate
1 small scoop of O6
495 μL MTBE+5 μL alcohol (1% v/v)
OR 487.5 μL MTBE+12.5 μL alcohol (2.5% v/v)

Four alcohols were investigated as nucleophile for the deacylation:
1-Butanol
1-Pentanol
1-Hexanol
1-Octanol Enzyme was added to the reaction vial first, followed by a stock solution of ingenol-3,20-diangelate in heptane and then the appropriate alcohol (either 12.5 μL or 5 μL).

Reactions were shaken at 50° C. for a total of 136 hours (6 days), with a 150 μL sample being taken for HPLC analysis after 64 hours followed by a final analysis.

A summary of results is shown in Table 32.

TABLE 31

Summary of results for deacylation screening reactions of ingenol-3,20-diangelate with O6 in MTBE containing butanol, pentanol, hexanol or octanol as nucleophile at 30° C.

| | | | HPLC ANALYSIS (% conversion) | | | |
|---|---|---|---|---|---|---|
| NUCLEOPHILE | % (v/v) NUCLEOPHILE | REACTION TIME (HOURS) | Ingenol | ingenol-3-angelate | PEP015 | PEP025 |
| 1-Butanol | 2.5 | 40 | 0 | 6.95 | 0 | 0 |
| | | 112 | 0 | 22.78 | 0 | 0 |
| | | 160 | 0 | 36.67 | 0 | 0 |
| | 5 | 40 | 0 | 1.90 | 0 | 0 |
| | | 112 | 0 | 5.45 | 0 | 0 |
| | | 160 | 0 | 8.90 | 0 | 0 |
| | 10 | 40 | 0 | 1.29 | 0 | 0 |
| | | 112 | 0 | 3.35 | 0 | 0 |
| | | 160 | 0 | 5.77 | 0 | 0 |
| 1-Pentanol | 2.5 | 40 | 0 | 3.86 | 0 | 0 |
| | | 112 | 0 | 12.88 | 0 | 0 |
| | | 160 | 0 | 22.72 | 0 | 0 |
| | 5 | 40 | 0 | 2.16 | 0 | 0 |
| | | 112 | 0 | 6.51 | 0 | 0 |
| | | 160 | 0 | 10.90 | 0 | 0 |
| | 10 | 40 | 0 | 0.80 | 0 | 0 |
| | | 112 | 0 | 2.48 | 0 | 0 |
| | | 160 | 0 | 4.02 | 0 | 0 |
| 1-Hexanol | 2.5 | 40 | 0 | 3.21 | 0 | 0 |
| | | 112 | 0 | 26.17 | 0 | 0 |
| | | 160 | 0 | 37.84 | 0 | 0 |
| | 5 | 40 | 0 | 1.52 | 0 | 0 |
| | | 112 | 0 | 5.37 | 0 | 0 |
| | | 160 | 0 | 8.95 | 0 | 0 |
| | 10 | 40 | 0 | 0.74 | 0 | 0 |
| | | 112 | 0 | 2.31 | 0 | 0 |
| | | 160 | 0 | 3.67 | 0 | 0 |
| 1-Octanol | 2.5 | 40 | 0 | 4.50 | 0 | 0 |
| | | 112 | 0 | 13.64 | 0 | 0 |
| | | 160 | 0 | 20.18 | 0 | 0 |
| | 5 | 40 | 0 | 2.55 | 0 | 0 |
| | | 112 | 0 | 12.68 | 0 | 0 |
| | | 160 | 0 | 21.05 | 0 | 0 |
| | 10 | 40 | 0 | 1.84 | 0 | 0 |
| | | 112 | 0 | 7.24 | 0 | 0 |
| | | 160 | 0 | 11.68 | 0 | 0 |

TABLE 32

Summary of results for deacylation screening reactions of ingenol-3,20-diangelate with 06 in heptane containing butanol, pentanol, hexanol or octanol as nucleophile at 50° C.

| NUCLEOPHILE | % (v/v) NUCLEOPHILE | REACTION TIME (HOURS) | HPLC ANALYSIS (% conversion) | | | |
|---|---|---|---|---|---|---|
| | | | Ingenol | ingenol-3-angelate | PEP015 | PEP025 |
| 1-Butanol | 1 | 64 | 0 | 82.73 | 0 | 0 |
| | | 136 | 0 | 96.51 | 0 | 0 |
| | 2.5 | 64 | 0 | 50.43 | 0 | 0 |
| | | 136 | 0 | 81.17 | 0 | 0 |
| 1-Pentanol | 1 | 64 | 0 | 70.34 | 0 | 0 |
| | | 136 | 0 | 93.14 | 0 | 0 |
| | 2.5 | 64 | 0 | 42.94 | 0 | 0 |
| | | 136 | 0 | 74.14 | 0 | 0 |
| 1-Hexanol | 1 | 64 | 0 | 87.38 | 0 | 0 |
| | | 136 | 0 | 99.02 | 0 | 0 |
| | 2.5 | 64 | 0 | 46.10 | 0 | 0 |
| | | 136 | 0 | 78.35 | 0 | 0 |
| 1-Octanol | 1 | 64 | 0 | 96.98 | 0 | 0 |
| | | 136 | 0 | 99.28 | 0 | 0 |
| | 2.5 | 64 | 0 | 71.90 | 0 | 0 |
| | | 136 | 0 | 95.62 | 0 | 0 |

Investigation of a One-Pot Synthesis of ingenol-3-angelate Via ingenol-3,20-diangelate The reaction contained the following:
8 mg Ingenol
2.5 eq. angelic anhydride 2 (10.48 mg)
5 small scoops of 54
8 pellets of 4 Å molecular sieves
50 mg CTAB (2.5% w/v)
2 mL heptane The reaction was shaken for 70 hours at 50° C., and then a 200 µL sample was taken for HPLC analysis.

(NOTE: For this experiment, solid surfactant was simply added to the reaction mixture, as with previous surfactant experiments with 54 (see Section 8). The enzyme was not pre-formulated by freeze-drying with a solution of surfactant.)

The result is summarized in Table 33.

TABLE 33

Summary of reaction of Ingenol with hydrolase 54 in heptane containing 2.5% (w/v) cationic surfactant.

| SURFACTANT | HPLC ANALYSIS (% conversion) | | | | | | |
|---|---|---|---|---|---|---|---|
| | ingenol-3-angelate | PEP015 | PEP025 | Cmpd 4 | 4.88 min | 5.19 min | 6.54 min |
| CTAB | 0.41 | 0 | 13.10 | 79.13 | 3.66 | 1.28 | 2.41 |

The remainder of the reaction mixture was filtered through a glass pipette containing a cotton wool plug to remove hydrolase 54. Hydrolase 06 was then added to the filtrate, along with octanol (20 µL, 1% v/v) and this was shaken at 50° C. to deacylate ingenol-3,20-diangelate to ingenol-3-angelate. Samples were taken for HPLC analysis after 21 hours and 44 hours (91 hours and 114 hours total reaction time, respectively). This data was plotted and shown in FIG. 1.

These previous screening experiments were carried out under very dilute conditions (1 mg substrate/reaction) with a high loading of enzyme (1 small scoop—not accurately measured). A small scoop of AH-06 was found to be ~20 mg, therefore the enzyme loading was ~2000% w/w with respect to substrate. Clearly this is an unacceptably high enzyme loading for scaled-up synthesis of PEP005. Therefore it was necessary to establish conditions that could accomplish the desired deacylation at higher substrate concentration and with lower enzyme loading.

The immediate aim for LEO was to determine exact experimental conditions that could demonstrate that the complete conversion of compound 4 to PEP005 could be achieved, and that PEP005 could be isolated in good yield. At this stage, optimized conditions were not required. This can be accomplished at a later stage.

1.4. Experiment ALM2232031

Initial 10 mg Reactions with AH-06

An initial set of six experiments were carried out at 10 mg scale (10 times screening concentration) and with 50% or 100% w/w loading of enzyme (significantly lower than screening reactions).

Reactions were carried out in HPLC vials and contained the following:
10 mg compound 4
Hydrolase AH-06 (50% or 100% w/w)
Octanol (1%, 2% or 5% v/v)
Heptane (0.5 mL)

Variations were as follows:

A) 5 mg AH-06 (50% w/w)+5 µL octanol (1% v/v)

B) 5 mg AH-06 (50% w/w)+10 µL octanol (2% v/v)

C) 5 mg AH-06 (50% w/w)+25 µL octanol (5% v/v)

D) 10 mg AH-06 (100% w/w)+5 µL octanol (1% v/v)

E) 10 mg AH-06 (100% w/w)+10 µL octanol (2% v/v)

F) 10 mg AH-06 (100% w/w)+25 µL octanol (5% v/v)

Reactions were shaken at 50° C. and sampled at intervals for HPLC analysis (Table 34).

All reactions exhibited very low conversions to PEP005. After 7 days, the highest conversion was only ~3.2%. It seems clear that 50% and 100% w/w loadings of enzyme AH-06 are too low.

TABLE 34

Summary of experiment ALM2232031 results.

| REACTION | REACTION TIME (HOURS) | HPLC ANALYSIS (% area) | |
|---|---|---|---|
| | | PEP005 | Cmpd 4 |
| A | 41 | 0.61 | 99.39 |
| | 115 | 0.93 | 99.07 |
| | 164 | 1.11 | 98.89 |
| B | 41 | 0.64 | 99.36 |
| | 115 | 1.06 | 98.94 |
| | 164 | 1.27 | 98.73 |
| C | 41 | 0.78 | 99.22 |
| | 115 | 1.36 | 98.64 |
| | 164 | 1.67 | 98.33 |
| D | 41 | 1.50 | 98.50 |
| | 115 | 1.91 | 98.09 |
| | 164 | 1.96 | 98.04 |
| E | 41 | 1.67 | 98.33 |
| | 115 | 2.34 | 97.66 |
| | 164 | 2.58 | 97.42 |
| F | 41 | 1.86 | 98.14 |
| | 115 | 2.89 | 97.11 |
| | 164 | 3.17 | 96.83 |

1.5. Experiment ALM2232035

2 mg Reactions with AH-06

A number of deacylation reactions were carried out at 2 mg scale with varying loadings of hydrolase AH-06. In addition, a repeat of the original screening reaction that previously gave the best rate of conversion to PEP005 was carried out to confirm reproducibility. All reactions were carried out in 0.5 mL heptane containing 5 µL octanol (1% v/v).

Reaction conditions were as follows:

G) Repeat of original screening reaction:

1 mg compound 4+1 small scoop of AH-06 (~20 mg).

H) 2 mg compound 4+4 mg AH-06 (200% w/w).

J) 2 mg compound 4+10 mg AH-06 (500% w/w).

K) 2 mg compound 4+20 mg AH-06 (1000% w/w).

L) 2 mg compound 4+30 mg AH-06 (1500% w/w).

Reactions were shaken at 50° C. and sampled at intervals for HPLC analysis (Table 35). Unfortunately the contents of reaction K leaked from the reaction vessel, so results were not available for 1000% w/w.

TABLE 35

Summary of experiment ALM2232035 results.

| REACTION | REACTION TIME (HOURS) | HPLC ANALYSIS (% area) | |
|---|---|---|---|
| | | PEP005 | Cmpd 4 |
| G | 68 | 67.40 | 32.60 |
| | 117 | 82.58 | 17.42 |
| | 164 | 90.33 | 9.67 |
| | 235 | 98.88 | 1.12 |
| H | 68 | 3.92 | 96.08 |
| | 117 | 4.44 | 95.56 |
| | 164 | 4.65 | 95.35 |
| | 235 | 4.90 | 95.10 |
| J | 68 | 15.19 | 84.81 |
| | 117 | 19.80 | 80.20 |
| | 164 | 22.83 | 77.17 |
| | 235 | 27.08 | 72.92 |
| L | 68 | 66.53 | 33.47 |
| | 117 | 81.49 | 18.51 |
| | 164 | 89.77 | 10.23 |
| | 235 | 98.69 | 1.31 |

Both reactions G and L reached >98% conversion to PEP005 after 10 days. However, reactions H (200% w/w enzyme) and 3 (500% w/w enzyme) only reached ~5% and ~27% conversion, respectively.

1.6. Experiment ALM2232039

5 mg & 10 mg Reactions with AH-06

Following on from experiment ALM2232035 (see Section 11.2), reactions were carried out at higher substrate concentration (either 5 mg or 10 mg/reaction) with either 500% or 1500% loading of hydrolase AH-06 (to directly compare to the results of experiments J and L). All reactions were carried out in 0.5 mL heptane.

Reaction conditions were as follows:

M) 5 mg compound 4+25 mg AH-06 (500% w/w)+5 µL octanol (1% v/v)

N) 10 mg compound 4+50 mg AH-06 (500% w/w)+5 µL octanol (1% v/v)

P) 5 mg compound 4+75 mg AH-06 (1500% w/w)+5 µL octanol (1% v/v)

R) 10 mg compound 4+150 mg AH-06 (1500% w/w)+5 µL octanol (1% v/v)

An additional two reactions were carried out to assess if changing the % of octanol had a significant effect on rate of reaction. These reactions are directly comparable to reaction M.

S) 5 mg compound 4+25 mg AH-06 (500% w/w)+2.5 µL octanol (0.5% v/v)

T) 5 mg compound 4+25 mg AH-06 (500% w/w)+12.5 µL octanol (2.5% v/v)

Reactions were shaken at 50° C. and sampled at intervals for HPLC analysis (Table 36).

Reactions M, N, S and T all proceeded at very similar rates, reaching ~40-45% conversion after 7 days. As expected, reactions P and R (with 1500% w/w enzyme loading) were significantly faster, with both reaching >95% conversion after 5 days. Reaction R (with 10 mg substrate) appeared to proceed at a faster rate than reaction P (with 5 mg substrate), and both of these were faster than reaction L (with 2 mg substrate). This indicates that a higher substrate concentration is preferable.

By comparing reactions M, S and T, there did not appear to be a significant correlation between octanol concentration (% v/v) and rate of reaction.

TABLE 36

Summary of experiment ALM2232039 results.

| REACTION | REACTION TIME (HOURS) | HPLC ANALYSIS (% area) | |
|---|---|---|---|
| | | PEP005 | Cmpd 4 |
| M | 40 | 17.95 | 82.05 |
| | 112 | 35.08 | 64.92 |
| | 160 | 40.18 | 59.82 |
| N | 40 | 21.31 | 78.69 |
| | 112 | 35.89 | 64.11 |
| | 160 | 40.87 | 59.13 |
| P | 40 | 63.81 | 36.19 |
| | 112 | 95.16 | 4.84 |
| | 160 | 97.20 | 2.80 |
| R | 40 | 78.08 | 21.92 |
| | 112 | 96.50 | 3.50 |
| | 160 | 95.81 | 4.19 |
| S | 40 | 19.18 | 80.82 |
| | 112 | 37.84 | 62.16 |
| | 160 | 44.02 | 55.98 |
| T | 40 | 18.25 | 81.75 |
| | 112 | 34.47 | 65.53 |
| | 160 | 41.04 | 58.96 |

1.7. Experiment ALM2232043

Additional Reactions with AH-09 & AH-24

Initial screening work identified three hydrolases that showed evidence of the selective deacylation of compound 4 to form desired product PEP005. These were AH-06, AH-09 and AH-24 (all three derived from *Candida rugosa*). During the previous phase of work (project 0741A0020B), AH-06 was selected for further investigation due to observed high conversions when using 5% (v/v) butanol as transesterification nucleophile. It was later discovered that 1% (v/v) octanol was a better nucleophile for the reaction.

Due to limited prior investigation with AH-09 and AH-24, it was decided to run some additional experiments with these enzymes with 5 mg compound 4 in 0.5 mL heptane in the presence of 1% (v/v) butanol, hexanol or octanol. Six reactions were carried out:

U) 25 mg AH-09 (500% w/w)+5 µL octanol (1% v/v)
V) 25 mg AH-24 (500% w/w)+5 µL octanol (1% v/v)
W) 25 mg AH-09 (500% w/w)+5 µL butanol (1% v/v)
X) 25 mg AH-24 (500% w/w)+5 µL butanol (1% v/v)
Y) 25 mg AH-09 (500% w/w)+5 µL hexanol (1% v/v)
Z) 25 mg AH-24 (500% w/w)+5 µL hexanol (1% v/v)

Reactions were shaken at 50° C. and sampled at intervals for HPLC analysis (Table 37).

TABLE 37

Summary of experiment ALM2232043 results.

| REACTION | REACTION TIME (HOURS) | HPLC ANALYSIS (% area) | |
|---|---|---|---|
| | | PEP005 | Cmpd 4 |
| U | 66 | 72.27 | 27.73 |
| | 113 | 87.86 | 12.14 |
| | 138 | 92.26 | 7.74 |
| V | 66 | 1.37 | 98.63 |
| | 113 | 1.50 | 98.50 |
| | 138 | 1.60 | 98.40 |
| W | 66 | 29.63 | 70.37 |
| | 113 | 43.17 | 56.83 |
| | 138 | 48.81 | 51.19 |
| X | 66 | 1.13 | 98.87 |
| | 113 | 1.89 | 98.11 |
| | 138 | 2.03 | 97.97 |
| Y | 66 | 35.93 | 64.07 |
| | 113 | 51.15 | 48.85 |
| | 138 | 57.37 | 42.63 |
| Z | 66 | 23.63 | 76.37 |
| | 113 | 32.59 | 67.41 |
| | 138 | 36.37 | 63.63 |

Reactions U, W and Y all showed conversion to PEP005, demonstrating that hydrolase AH-09 was able to accept octanol, hexanol and butanol as transesterification nucleophile. As with AH-06, octanol was found to be the best nucleophile (reaction U) with ~92% conversion being achieved after 6 days. The equivalent reaction with AH-06 (500% w/w loading) only reached 35-40% conversion after 6 days. Indeed, to reach >90% conversion with AH-06 in the same time, a much higher loading of 1500% (w/w) was required.

Therefore it is clear that AH-09 is a more efficient enzyme for the selective deacylation of compound 4, giving significantly higher rates of reaction than the equivalent loading of AH-06.

Reactions V, X and Z showed that AH-24 does not accept octanol or hexanol as transesterification nucleophile for the reaction, but it does accept butanol. However, the rate of reaction is significantly slower than with AH-09 and octanol.

1.8. Experiment ALM2232047

Further Reactions with AH-09

Experiment ALM2232043 (reaction U) showed that hydrolase AH-09 is a more efficient enzyme than AH-06 for the deacylation of compound 4. Therefore a number of follow-up experiments were carried out to further investigate this. Reactions AA and AB were the same as reaction U, but with different amounts of octanol (0.5% and 2.5% v/v, respectively). Reaction AC had double the substrate concentration of reaction U. All reactions were carried out in 0.5 mL heptane:

AA) 5 mg compound 4+25 mg AH-09 (500% w/w)+2.5 µL octanol (0.5% v/v)
AB) 5 mg compound 4+25 mg AH-09 (500% w/w)+12.5 µL octanol (2.5% v/v)
AC) 10 mg compound 4+50 mg AH-09 (500% w/w)+5 µL octanol (1% v/v)

Reactions were shaken at 50° C. and sampled at intervals for HPLC analysis (Table 38).

TABLE 38

Summary of experiment ALM2232047 results.

| REACTION | REACTION TIME (HOURS) | HPLC ANALYSIS (% area) | |
|---|---|---|---|
| | | PEP005 | Cmpd 4 |
| AA | 41 | 90.65 | 9.35 |
| | 66 | 95.72 | 4.28 |

TABLE 38-continued

Summary of experiment ALM2232047 results.

| REACTION | REACTION TIME (HOURS) | HPLC ANALYSIS (% area) | |
|---|---|---|---|
| | | PEP005 | Cmpd 4 |
| AB | 41 | 85.25 | 14.75 |
| | 66 | 94.96 | 5.04 |
| AC | 41 | 94.07 | 5.93 |
| | 66 | 96.74 | 3.26 |

All three reactions proceeded very well, reaching ~95% conversion to PEP005 after 66 hours. This was faster than any previously observed reactions. The difference in rate between each reaction was minor, although the best was achieved with reaction AC, which had double the substrate concentration (10 mg/reaction). This implies that higher substrate concentration is beneficial to reaction rate.

Reactions AA and AB were intended to be directly comparable to reaction U (experiment ALM2232043), but both showed markedly faster reaction rates. It is not believed that this is due to the differences in octanol loading, but rather that reaction U was carried out using an older sample of hydrolase AH-09.

It was decided to adapt the conditions of reaction AC for a >100 mg scale-up experiment.

1.9. Experiment ALM2232051

Scale-Up Reaction & Isolation of PEP005

A 123.9 mg scale enzymatic deacylation of compound 4 was carried out with subsequent isolation of PEP005. Reaction conditions were adapted from those used for reaction AC (experiment ALM2232047).

Compound 4 (123.9 mg, 0.242 mmol) and hydrolase AH-09 (620 mg, 500% w/w) were measured into an 8 mL glass vial. Heptane (5 mL) was added, followed by 1-octanol (50 μL, 1% v/v). The vial was sealed tightly and shaken at 50° C. in an orbital incubator at 190 rpm. Samples (20 μL) were taken daily for HPLC analysis to monitor reaction progress. After 71 hours, the reaction had reached 97% conversion. Silica chromatography was carried out (eluent gradient from 100% hexane to 3:2 hexane/EtOAc) to afford a clear glassy solid which was left under vacuum overnight to remove solvent traces. Upon scraping, this afforded PEP005 as a white solid (95 mg, 0.221 mmol, 91% yield—ALM2232051-1).

Final HPLC analysis of this material was carried out and compared to a blank sample (both made up in the same batch of 1:1 25 mM $KH_2PO_4$ (pH 2.2)/acetonitrile. All peaks that did not appear in the blank trace were integrated to give a final PEP005 percentage area of 96.97%

$^1$H NMR analysis of ALM2232051-1 looked as expected. Importantly, the undesired isomerisation of angelate to tiglate did not occur under the enzymatic reaction conditions

The invention claimed is:

1. A method for preparation of ingenol-3-angelate, comprising:
   acylating ingenol with angeloyl at the 3-position and acylating the 20-position with either angeloyl or another group to obtain a 3, 20-diacylated ingenol derivative; and
   deacylating the 3, 20-diacylated ingenol derivative with a hydrolase to selectively deacylate the ingenol derivative at the 20-position, to obtain ingenol-3-angelate.

2. The method of claim 1, wherein 3, 20-diacylated ingenol derivative is ingenol-3,20-di-angelate.

3. The method of claim 1, wherein the hydrolase is Lipase B from *Candida rugosa*.

4. The method of claim 1 wherein the hydrolase is present in more than 100% w/w loading of the enzymes relative to the 3, 20-diacylated ingenol derivative.

5. The method of claim 1, wherein the reaction is performed in the presence of an organic solvent, wherein the organic solvent is heptane.

6. The method of claim 1, wherein the reaction is performed in the presence of a nucleophile.

7. The method of claim 6, wherein the nucleophile is present in a concentration below about 10% v/v.

8. The method of claim 7, wherein the nucleophile is present in a concentration of less than about 5% v/v.

9. The method of claim 6, wherein the nucleophile is water or an alcohol selected from a group of alcohols consisting of 1-butanol, 1-pentanol, 1-hexanol and 1-octanol.

10. The method of claim 9, wherein the nucleophile is 1-octanol.

11. The method of claim 10, wherein the nucleophile is present in a concentration of less than about 10% v/v.

12. The method of claim 11, wherein the nucleophile is present in a concentration of less than about 5% v/v.

13. The method of claim 9, wherein the nucleophile is present in a concentration of less than about 10% v/v.

14. The method of claim 13, wherein the nucleophile is present in a concentration of less than about 5% v/v.

15. The method of claim 1, wherein the preparation of the diacylated ingenol derivative is prepared by reacting ingenol in the presence of an acyl donor and optionally a hydrolase.

16. The method of claim 15, wherein the acyl donor is angelic anhydride.

17. The method of claim 16, wherein the acyl donor is added in 4 equivalents.

18. The method of claim 17, wherein the reaction is performed at elevated temperatures.

19. The method of claim 18, wherein the temperature is about 50° C.

20. The method of claim 16, wherein the reaction is performed at elevated temperatures.

21. The method of claim 20, wherein the temperature is about 50° C.

22. The method of claim 15, wherein the hydrolase is selected from a group of Lipase B enzymes consisting of Lipase B from *Alcaligenes* sp., Lipase B from *Candida rugosa*, or Lipase B from *Burkholderia cepacia*.

23. The method of claim 15, wherein the reaction is performed in an organic solvent.

24. The method of claim 23, wherein the solvent is heptane.

25. The method of claim 15, wherein the diacylated ingenol derivative is ingenol-3,20-diangelate.

26. The method of claim 15, wherein the reaction is performed at elevated temperatures.

27. The method of claim 26, wherein the temperature is about 50° C.

* * * * *